US006538080B1

(12) United States Patent
Swindoll et al.

(10) Patent No.: US 6,538,080 B1
(45) Date of Patent: *Mar. 25, 2003

(54) GAS PHASE POLYMERIZATION OF OLEFINS

(75) Inventors: Robert D. Swindoll, Richwood, TX (US); Bruce A. Story, Lake Jackson, TX (US); Brian W. S. Kolthammer, Lake Jackson, TX (US); Kevin P. Peil, Auburn, MI (US); David R. Wilson, Midland, MI (US); James C. Stevens, Richmond, TX (US)

(73) Assignee: BP Chemicals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/498,912

(22) Filed: Feb. 4, 2000

Related U.S. Application Data

(63) Continuation of application No. 08/659,976, filed on Jun. 3, 1996, now Pat. No. 6,025,448, which is a continuation-in-part of application No. 08/308,068, filed on Sep. 16, 1994, now abandoned, which is a continuation-in-part of application No. 08/122,852, filed on Sep. 17, 1993, now abandoned, which is a continuation-in-part of application No. 08/475,737, filed on Jun. 7, 1995, now abandoned, which is a continuation-in-part of application No. 08/378,998, filed on Jan. 27, 1995, now abandoned, which is a continuation-in-part of application No. 08/054,379, filed on Apr. 28, 1993, now abandoned, which is a division of application No. 07/776,130, filed on Oct. 15, 1991, now Pat. No. 5,272,236, which is a continuation-in-part of application No. 08/510,527, filed on Aug. 2, 1995, now abandoned, which is a continuation of application No. 08/010,958, filed on Jan. 29, 1993, now abandoned, which is a continuation-in-part of application No. 08/208,068, filed on Mar. 8, 1994, now abandoned, which is a continuation of application No. 07/815,716, filed on Dec. 30, 1991, now abandoned, which is a continuation-in-part of application No. 08/433,785, filed on May 3, 1995, now abandoned, which is a division of application No. 08/208,068, filed on Mar. 8, 1994, now abandoned, which is a continuation-in-part of application No. 07/545,403, filed on Jul. 3, 1990, now abandoned, and a continuation-in-part of application No. 08/626,303, filed on Apr. 1, 1996, now Pat. No. 5,763,547.

(51) Int. Cl.$^7$ .................................................. C08F 4/42
(52) U.S. Cl. ..................... 526/160; 526/127; 526/65; 526/129; 526/901; 526/280; 526/281; 526/282; 526/943; 502/155; 502/120; 525/53
(58) Field of Search .................. 526/127, 65, 129, 526/160, 901, 280, 281, 282, 943; 502/155, 120; 525/53

(56) References Cited

U.S. PATENT DOCUMENTS

| | | |
|---|---|---|
| 3,491,073 A | 1/1970 | Marinak |
| 3,645,992 A | 2/1972 | Elston |

(List continued on next page.)

FOREIGN PATENT DOCUMENTS

| | | |
|---|---|---|
| BE | 839380 | 9/1976 |
| CA | 991798 | 6/1976 |

(List continued on next page.)

OTHER PUBLICATIONS

US 5,168,111, 12/1992, Canich (withdrawn)

(List continued on next page.)

*Primary Examiner*—David W. Wu
*Assistant Examiner*—Ling-Siu Choi
(74) *Attorney, Agent, or Firm*—Finnegan, Henderson, Farabow, Garrett and Dunner, L.L.P.

(57) ABSTRACT

A gas phase fluidized bed process is described for producing ethylene polymers having improved processability and an MWD of less than about 2.9. Multiple reactors in series or parallel may be used to produce in-situ blended polymers. Each reactor can separately have a constrained geometry catalyst or a conventional Ziegler-Natta catalyst as needed for obtaining in-situ blended polymer with the desired properties as long as there is a constrained geometry catalyst in at least one reactor. Olefin polymers can be produced according to this invention which have low susceptibility to melt fracture, even under high shear stress conditions.

24 Claims, 1 Drawing Sheet

LDPE

LLDPE

HOMOGENEOUS COPOLYMERS

SUBSTANTIALLY LINEAR ETHYLENE POLYMERS

U.S. PATENT DOCUMENTS

| | | |
|---|---|---|
| 3,709,853 A | 1/1973 | Karapinka .................. 260/88.2 |
| 3,914,342 A | 10/1975 | Mitchell .................. 260/897 A |
| 4,003,712 A | 1/1977 | Miller ...................... 23/288 S |
| 4,011,382 A | 3/1977 | Levine et al. ............... 526/9 B |
| 4,011,384 A | 3/1977 | Baxmann et al. |
| 4,076,698 A | 2/1978 | Anderson et al. ........ 526/348.6 |
| 4,205,021 A | 5/1980 | Morita et al. |
| 4,259,468 A | 3/1981 | Kajiura et al. |
| 4,302,565 A | 11/1981 | Goeke et al. .................. 526/88 |
| 4,302,566 A | 11/1981 | Karol et al. |
| 4,303,710 A | 12/1981 | Bullard et al. |
| 4,303,771 A | 12/1981 | Wagner et al. |
| 4,328,328 A | 5/1982 | Minami et al. |
| 4,339,493 A | 7/1982 | Weiner |
| 4,339,496 A | 7/1982 | Weiner |
| 4,340,640 A | 7/1982 | Weiner |
| 4,340,641 A | 7/1982 | Weiner |
| 4,343,926 A | 8/1982 | Caumartin et al. ........... 526/68 |
| 4,346,834 A | 8/1982 | Mazumdar |
| 4,349,648 A | 9/1982 | Iorgensen et al. |
| 4,354,009 A | 10/1982 | Goeke et al. |
| 4,359,561 A | 11/1982 | Fraser et al. |
| 4,363,904 A | 12/1982 | Fraser et al. |
| 4,367,256 A | 1/1983 | Biel |
| 4,370,456 A | 1/1983 | George |
| 4,379,197 A | 4/1983 | Cipriani et al. |
| 4,380,567 A | 4/1983 | Shigemoto |
| 4,383,095 A | 5/1983 | Goeke et al. |
| 4,390,677 A | 6/1983 | Karol et al. |
| 4,395,359 A | 7/1983 | Wagner et al. .......... 252/429 B |
| 4,399,180 A | 8/1983 | Briggs |
| 4,404,344 A | 9/1983 | Sinn et al. |
| 4,405,495 A | 9/1983 | Lee et al. ............... 252/429 B |
| 4,405,774 A | 9/1983 | Miwa et al. |
| 4,410,649 A | 10/1983 | Cieloszyk |
| 4,418,114 A | 11/1983 | Briggs et al. |
| 4,424,138 A | 1/1984 | Candlin et al. |
| 4,427,573 A | 1/1984 | Miles et al. |
| 4,431,788 A | 2/1984 | Kaminsky |
| 4,438,243 A | 3/1984 | Kashiwa et al. |
| 4,452,958 A | 6/1984 | Chester et al. |
| 4,454,281 A | 6/1984 | Heitz et al. |
| 4,461,792 A | 7/1984 | Anthony |
| 4,463,153 A | 7/1984 | Mizutani et al. |
| 4,464,426 A | 8/1984 | Anthony |
| 4,467,065 A | 8/1984 | Williams et al. |
| 4,474,740 A | 10/1984 | Karwat et al. |
| 4,481,301 A | 11/1984 | Nowlin et al. ............... 502/104 |
| 4,482,687 A | 11/1984 | Noshay et al. |
| 4,485,217 A | 11/1984 | Gunter et al. |
| 4,486,579 A | 12/1984 | Machon et al. |
| 4,500,648 A | 2/1985 | Malpass .................... 502/115 |
| 4,505,970 A | 3/1985 | Craver |
| 4,510,303 A | 4/1985 | Oda et al. |
| 4,513,038 A | 4/1985 | Anthony |
| 4,514,465 A | 4/1985 | Schoenberg |
| 4,519,968 A | 5/1985 | Klaus et al. |
| 4,530,914 A | 7/1985 | Ewen et al. |
| 4,532,189 A | 7/1985 | Mueller |
| 4,542,199 A | 9/1985 | Kaminsky et al. |
| 4,543,399 A | 9/1985 | Jenkins, III et al. .......... 526/70 |
| 4,544,762 A | 10/1985 | Kaminsky et al. .......... 556/179 |
| 4,547,555 A | 10/1985 | Cook et al. |
| 4,551,380 A | 11/1985 | Schoenberg |
| 4,562,169 A | 12/1985 | Hagerty et al. ............. 502/107 |
| 4,563,504 A | 1/1986 | Hert et al. |
| 4,564,559 A | 1/1986 | Wagner |
| 4,568,713 A | 2/1986 | Hansen et al. |
| 4,587,318 A | 5/1986 | Inoue et al. |
| 4,588,650 A | 5/1986 | Mientus et al. |
| 4,588,790 A | 5/1986 | Jenkins, III et al. .......... 526/70 |
| 4,588,794 A | 5/1986 | Oda |
| 4,593,009 A | 6/1986 | Nowlin |
| 4,597,920 A | 7/1986 | Golike |
| 4,598,128 A | 7/1986 | James et al. |
| 4,599,391 A | 7/1986 | Yamamoto et al. |
| 4,613,547 A | 9/1986 | Wagner et al. |
| 4,617,241 A | 10/1986 | Mueller |
| 4,618,662 A | 10/1986 | Nowlin |
| 4,624,991 A | 11/1986 | Haas |
| 4,626,467 A | 12/1986 | Hostetter |
| 4,629,771 A | 12/1986 | Candlin et al. |
| 4,649,001 A | 3/1987 | Nakamura et al. |
| 4,665,046 A | 5/1987 | Campbell |
| 4,666,772 A | 5/1987 | Schinkel et al. |
| 4,666,999 A | 5/1987 | Cook et al. |
| 4,668,575 A | 5/1987 | Schinkel et al. |
| 4,668,650 A | 5/1987 | Lo et al. |
| 4,668,752 A | 5/1987 | Tominari et al. |
| 4,672,096 A | 6/1987 | Nowlin |
| 4,676,922 A | 6/1987 | Sommer |
| 4,677,087 A | 6/1987 | Lo et al. |
| 4,680,353 A | 7/1987 | Ishihara et al. |
| 4,690,991 A | 9/1987 | Seppl |
| 4,690,992 A | 9/1987 | Grubbs et al. |
| 4,692,386 A | 9/1987 | Schinkel et al. |
| 4,701,432 A | 10/1987 | Welborn, Jr. ................ 502/113 |
| 4,703,094 A | 10/1987 | Raufast ...................... 526/65 |
| 4,710,538 A | 12/1987 | Jorgensen |
| 4,716,207 A | 12/1987 | Cozewith et al. |
| 4,719,193 A | 1/1988 | Levine et al. |
| 4,720,427 A | 1/1988 | Clauson et al. |
| 4,722,971 A | 2/1988 | Datta et al. |
| 4,732,882 A | 3/1988 | Allen et al. |
| 4,742,138 A | 5/1988 | Kageyama |
| 4,762,898 A | 8/1988 | Matsuura et al. |
| 4,764,549 A | 8/1988 | Greenhalgh et al. |
| 4,775,710 A | 10/1988 | Dunski et al. |
| 4,780,264 A | 10/1988 | Dohrer et al. |
| 4,788,232 A | 11/1988 | Needham |
| 4,789,714 A | 12/1988 | Cozewith et al. |
| 4,792,595 A | 12/1988 | Cozewith et al. |
| 4,794,096 A | 12/1988 | Ewen |
| 4,798,081 A | 1/1989 | Hazlitt et al. ................... 73/53 |
| 4,803,253 A | 2/1989 | McDaniel et al. |
| 4,808,561 A | 2/1989 | Welburn, Jr. |
| 4,808,635 A | 2/1989 | Nguyen |
| 4,820,471 A | 4/1989 | Van der Molten |
| 4,820,589 A | 4/1989 | Dobreski et al. |
| 4,824,889 A | 4/1989 | Mostert |
| 4,826,939 A | 5/1989 | Stuart |
| 4,830,926 A | 5/1989 | Mostert |
| 4,833,017 A | 5/1989 | Benoit |
| 4,833,224 A | 5/1989 | Tanaka et al. |
| 4,834,947 A | 5/1989 | Cook et al. |
| 4,842,187 A | 6/1989 | Janocha et al. |
| 4,842,930 A | 6/1989 | Schinkel |
| 4,842,951 A | 6/1989 | Yamada et al. |
| 4,857,761 A | 8/1989 | Durand et al. |
| 4,871,705 A | 10/1989 | Hoel |
| 4,874,734 A | 10/1989 | Kiora et al. |
| 4,874,820 A | 10/1989 | Cozewith et al. |
| 4,876,321 A | 10/1989 | Lo et al. |
| 4,882,406 A | 11/1989 | Cozewith et al. |
| 4,883,853 A | 11/1989 | Hobes et al. |
| 4,888,318 A | 12/1989 | Allen et al. |
| 4,892,911 A | 1/1990 | Genske |
| 4,897,455 A | 1/1990 | Welborn, Jr. ............... 526/129 |
| 4,914,253 A | 4/1990 | Chang ........................ 585/523 |
| 4,921,920 A | 5/1990 | Collomb Ceccarini et al. |
| 4,923,750 A | 5/1990 | Jones |

| | | | |
|---|---|---|---|
| 4,923,833 A | 5/1990 | Kioka et al. | |
| 4,925,728 A | 5/1990 | Crass et al. | |
| 4,931,517 A | 6/1990 | Fujita | 526/128 |
| 4,935,474 A | 6/1990 | Ewen et al. | |
| 4,937,299 A | 6/1990 | Ewen et al. | |
| 4,937,301 A | 6/1990 | Chang | 526/128 |
| 4,950,724 A | 8/1990 | Malanga et al. | |
| 4,959,436 A | 9/1990 | Cozewith et al. | |
| 4,960,878 A | 10/1990 | Crapo et al. | 556/179 |
| 4,963,388 A | 10/1990 | Benoit | |
| 4,966,951 A | 10/1990 | Benham et al. | |
| 4,968,765 A | 11/1990 | Yagi et al. | |
| 4,975,315 A | 12/1990 | Bolthe et al. | |
| 4,976,898 A | 12/1990 | Lustig et al. | |
| 4,981,826 A | 1/1991 | Speca | |
| 4,983,447 A | 1/1991 | Crass et al. | |
| 4,987,212 A | 1/1991 | Morterol et al. | |
| 4,996,094 A | 2/1991 | Dutt | |
| 5,001,205 A | 3/1991 | Hoel | 526/128 |
| 5,006,396 A | 4/1991 | VanBortel et al. | |
| 5,013,801 A | 5/1991 | Cozewith et al. | |
| 5,015,511 A | 5/1991 | Treybig et al. | |
| 5,015,749 A | 5/1991 | Schmidt et al. | 556/179 |
| 5,017,665 A | 5/1991 | Chang | 526/129 |
| 5,019,315 A | 5/1991 | Wilson | |
| 5,024,799 A | 6/1991 | Harp et al. | |
| 5,025,072 A | 6/1991 | Nowlin et al. | |
| 5,026,797 A | 6/1991 | Takahashi | 526/124 |
| 5,026,798 A | 6/1991 | Canich | |
| 5,041,316 A | 8/1991 | Parnell et al. | |
| 5,041,583 A | 8/1991 | Sangokoya | 556/179 |
| 5,041,584 A | 8/1991 | Crapo et al. | 556/179 |
| 5,041,585 A | 8/1991 | Deavenport et al. | 556/179 |
| 5,043,040 A | 8/1991 | Butler | |
| RE33,683 E | 9/1991 | Allen et al. | |
| 5,047,468 A | 9/1991 | Lee et al. | |
| 5,055,338 A | 10/1991 | Sheth et al. | |
| 5,055,438 A | 10/1991 | Canich | 502/117 |
| 5,055,533 A | 10/1991 | Allen et al. | |
| 5,055,534 A | 10/1991 | Theobald | |
| 5,057,475 A | 10/1991 | Canich et al. | 502/104 |
| 5,059,481 A | 10/1991 | Lustig et al. | |
| 5,064,796 A | 11/1991 | Speca | |
| 5,064,802 A | 11/1991 | Stevens et al. | 502/155 |
| 5,068,489 A | 11/1991 | Edwards et al. | |
| 5,073,452 A | 12/1991 | Satou et al. | |
| 5,073,599 A | 12/1991 | Genske | |
| 5,077,255 A | 12/1991 | Welbourn | 502/104 |
| 5,082,908 A | 1/1992 | Imai et al. | |
| 5,084,039 A | 1/1992 | Cancio et al. | |
| 5,084,534 A | 1/1992 | Welborn, Jr. et al. | 526/160 |
| 5,084,540 A | 1/1992 | Albizzati et al. | |
| 5,084,927 A | 2/1992 | Parkevich | |
| 5,096,867 A | 3/1992 | Canich | 502/103 |
| 5,106,804 A | 4/1992 | Bailly et al. | 502/108 |
| 5,126,398 A | 6/1992 | Lee et al. | 525/53 |
| 5,132,380 A | 7/1992 | Stevens et al. | 526/129 |
| 5,149,738 A | 9/1992 | Lee et al. | 525/53 |
| 5,171,799 A | 12/1992 | Kioka et al. | 26/127 |
| 5,189,192 A | 2/1993 | LaPointe et al. | 526/11 |
| 5,227,440 A | 7/1993 | Canich et al. | 526/129 |
| 5,238,892 A | 8/1993 | Chang | 502/111 |
| 5,240,894 A | 8/1993 | Burkhardt et al. | 502/108 |
| 5,241,025 A | 8/1993 | Hlatky et al. | 526/129 |
| 5,272,236 A | 12/1993 | Lai et al. | 526/348.5 |
| 5,278,272 A | 1/1994 | Lai et al. | 526/348.5 |
| 5,281,679 A | 1/1994 | Jejelowo et al. | 526/114 |
| 5,296,433 A | 3/1994 | Seidle et al. | 502/117 |
| 5,296,565 A | 3/1994 | Ueda et al. | 526/114 |
| 5,317,036 A | 5/1994 | Brady, III et al. | 523/223 |
| 5,324,800 A | 6/1994 | Welborn, Jr. et al. | 526/160 |
| 5,352,749 A | 10/1994 | DeChellis et al. | 526/68 |
| 5,373,072 A | 12/1994 | Chang | 526/129 |
| 5,374,696 A | 12/1994 | Rosen et al. | 526/126 |
| 5,382,638 A | 1/1995 | Bontemps et al. | 526/67 |
| 5,387,749 A | 2/1995 | Govoni et al. | 525/53 |
| 5,395,810 A | 3/1995 | Shamshoum et al. | 502/113 |
| 5,405,922 A | 4/1995 | DeChellis et al. | 526/68 |
| 5,420,220 A | 5/1995 | Cheruvu et al. | 526/348.1 |
| 5,436,304 A | 7/1995 | Griffin et al. | 526/68 |
| 5,444,145 A | 8/1995 | Brant et al. | 526/348.3 |
| 5,453,410 A | 9/1995 | Kolthammer et al. | 502/155 |
| 5,453,471 A | 9/1995 | Bernier et al. | 526/68 |
| 5,462,999 A | 10/1995 | Griffin et al. | 526/68 |
| 5,470,993 A | 11/1995 | Devore et al. | 556/11 |
| 5,541,270 A * | 7/1996 | Chinh et al. | 526/68 |
| 5,608,019 A | 3/1997 | Cheruvu et al. | 526/129 |
| 5,616,665 A | 4/1997 | Jejelowo et al. | 526/129 |
| 5,672,669 A | 9/1997 | Wasserman et al. | 526/170 |
| 5,712,352 A | 1/1998 | Brant et al. | 526/68 |
| 5,763,543 A | 6/1998 | Muhle et al. | 526/68 |
| 5,763,547 A * | 6/1998 | Kolthammer et al. | 526/129 |
| 5,783,645 A | 7/1998 | Baker et al. | 526/88 |
| 5,798,427 A | 8/1998 | Foster et al. | 526/352 |
| 5,804,678 A | 9/1998 | Morita et al. | 526/80 |
| 5,834,571 A | 11/1998 | Bernier et al. | 526/88 |
| 5,840,815 A | 11/1998 | Tsutsui et al. | 526/127 |
| 5,844,055 A | 12/1998 | Brandt et al. | 526/127 |

FOREIGN PATENT DOCUMENTS

| | | | |
|---|---|---|---|
| EP | 200 351 | 11/1986 | |
| EP | 273 654 | 7/1988 | |
| EP | 277 003 | 8/1988 | |
| EP | 0 336 593 | 10/1989 | C08F/4/60 |
| EP | 416815 | 3/1991 | |
| EP | 0416815 A2 | 3/1991 | |
| EP | 468651 | 1/1992 | |
| EP | 514828 | 11/1992 | |
| EP | 520 732 | 12/1992 | |
| EP | 0 634 421 A1 | 1/1995 | |
| EP | 0 659 773 A1 | 6/1995 | |
| JP | 73759 | 6/1979 | |
| SU | 176583 | 11/1965 | |
| WO | WO 9003414 | 4/1990 | |
| WO | 93 08221 | 4/1993 | C08F/10/00 |
| WO | 94 03506 | 2/1994 | C08F/4/64 |
| WO | 94 03509 | 2/1994 | C08F/210/16 |
| WO | 94 07928 | 4/1994 | C08F/10/02 |
| WO | 94/26816 | 11/1994 | C08L/23/08 |

OTHER PUBLICATIONS

Journal of Polymer Science. Part A, vol. 1 (pp. 2869–2880) (1963), "Long–Chain Branching Frequency in Polyethylene" by J.E. Guillet.

Polymer Preprints, Amer. Chem. Society, vol. 12, No. 1, pp. 277–281 (Mar. 1971), Evidence of Long–Chain Branching in High Density Polyethylene by E.E. Drott & R.A. Mendelson.

*Journal of the American Chemical Society*, 98–7, pp. 1729–1742 (Mar. 31, 1976) "Structure and Chemistry of Bis(cyclopentadienyl)—MLn Complexes" by Joseph W. Lauher and Ronald Hoffman.

*Polymer Engineering and Science*, vol. 16, No. 12, pp. 811–816 (Dec. 1976) "Influence of Long Chain Branching on the Viscoelastic Properties of Low–Density Polyethylenes" by L. Wild, R. Ranganath, and D. Knobeloch.

*Angew, Chem. Int. Ed. Engl.* pp. 630–632 (1976) vol. 15, No. 10, "Halogen Free Soluble Ziegler Catalysts for the Polymerization of Ethylene. Control of Molecular Weight by Choice of Temperature" by Arne Andresen et al.

Burdett, Ian D., *Chemtech*, "A continuing success: The UNIPOL process", Oct., 1992, pp. 616–623.

Furtek, A.B., *MetCon '93*, "Ultra Strength Polyethylene Resins Produced in a Fluid–Bed Process Utilizing Metallocene–Based Catalysts", May 28, 1993, pp. 125–137.

"Mobil makes 'ultra strength' PE", European Chemical News 7, Jun. 1993, p. 31.

"Extra–Tough, New Generation LLDPE Said to Mimic LDPE Processability", *Plastics Technology*, Apr. 1993, pp. 45–47.

"The Single–Site Polyolefin Story Continues to Unfold", *Plastics Technology*, Nov. 1993, pp. 27–29.

"New gas–phase metallocene LLDPEs are coming", *Plastics Formulating & Compounding*, Nov./Dec. 1995, pp. 5–7.

Xie, Tuyu, et al., "Gas Phase Ethylene Polymerization: Production Processes, Polymer Properties, and Reactor Modeling", *Ind. Eng. Chem. Res.*, vol. 33, No. 3 (1994), pp. 449–479.

"Exxon Devotes PE Unit to Exxpol Catalyst Tech.," European Chemical News, Apr. 6, 1992, vol. 57, No. 1514, p. 27.

"Exxon/Mitsui Sign R&D Deal from SSC Process," European Chemical News Apr. 27, 1992, vol. 57, No. 1517, p. 24.

"The Polyolefin Revolution—New Catalysts Pave Way for Differentiation," Chemical Week, May 13, 1992, pp. 52–53.

Yang et al., "Cation–like" Homogeneous Olefin Polymerization Catalysts Based upon Zirconocene Alkyls and Tri(p-entafluorophenyl)borane, J. Am. Chem. Soc. 1991 113, pp. 3623–3625.

*Advances in Organometallic Chemistry*, pp. 99–148, vol. 18, (1980) "Ziegler—Natta Catalysis" by Hansjorg Sinn and Walter Kaminsky.

*Angew. Chem Int. Ed. Engl.*, pp. 390–393, vol. 19, No. 5, (1980) "Living Polymers on Polymerization with Extremely Productive Ziegler Catalysts" by Hansjorg Sinn, Walter Kaminsky, Hans–Jurgen Vollmer, and Rudiger Woldt.

*Polymer Bulletin*, vol. 9, pp. 464–469 (1983) "Halogen Free Soluble Ziegler Catalysts with Methylalumoxan as Catalysts" by Jens Herwig and Walter Kaminsky.

*Makromol. Chem. Rapid Commun.*, vol. 4, pp. 417–421 (1983) "Bis(Cyclopentadienyl)zirkon–Verbingungen und Aluminoxan als Ziegler–Katalysatoren fur die Polymerisation und copolymerisation von Olefinen" by Walter Kaminsky et al.

*ANTEC Proceedings*, pp. 306–309 (1983), "Analysis of Long Chain Branching in High Density Polyethylene" by J.K. Hughes.

*Makromol. Chem. Rapid Commun.*, vol. 5, pp. 225–228 (1984) "Influence of hydrogen on the polymerization of ethylene with the homogeneous Ziegler system bis(cyclopentadienyl) zirconiumdichloride/aluminoxane" by Walter Kaminsky et al.

*Journal of Polymer Science, Polymer Chemistry Edition*, vol. 23, pp. 2117–2133 (1985) "Homogeneous Ziegler Natta Catalysis. 11. Ethylene Polymerization by IVB Transition Metal Complexes/Methyl Aluminoxane Catalyst Systems" by E. Giannetti and R. Mazzochi.

*Journal of Applied Polymer Science*, vol. 30, pp. 3751–3765 (1985) "On the Effects of Very Low Levels of Long Chain Branching on Rheological Behavior in Polyethylene" by B.H. Bersted.

*Journal of Polymer Science: Polymer Chemistry Edition*, vol. 23, pp. 2151–2164 (1985) "Ethylene Propylene Diene Terpolymers Produced with a Homogenous and Highly Active Zirconium Catalyst" by Walter Kaminsky et al.

*The Society of Rheology*, vol. 30, pp. 337–357, (1986) "Wall Slip in Viscous Fluids and the Influence of Materials of Construction" by A.V. Ramamurthy.

*Makromol. Chem. Macromol. Symp.* vol. 4, pp. 103–118, (1986) "Elastomers by Atactic Linkage of α–Olefins Using Soluble Ziegler Catalysts" by W. Kaminsky and M. Schlobohm.

*Journal of Rheology*, vol. 31, No. 8, pp. 815–834 (1987) "Wall Slip and Extrudate Distortion in Linear Low Density Polyethylene" by D. Kalika and M. Denn.

*Advances in Polyolefins*, by R.B. Seymour and T. Cheng, (1987) "Polymerization of Olefins with a Homogeeous Zirconium/Aluminoxane Catalyst" pp. 361–371 by W. Kaminsky and H. Hahnsen.

J.E. Bercaw, Southwestern Regional ACS Meeting, Corpus Christi, TX, Nov. 30, 1988, Talk #47 (abstract).

J.E. Bercaw, Division of Inorganice Chemistry, summer newsletter, May 1989, talk #233 (abstract).

Macromolecules, 22(7), 2875–2878 (1989).

Polymer Bulletin, 20, 237–241 (1988).

Organometallics, 6, 232–241 (1987).

K. Soga e. Polymer Bulletin 1988, 20, 237–241, CA 109(24):211425k.

Lu Zejian, Gaofenzi Xuebao, 1988(4), 268–273, CA 110:95856k.

A.A. Baulin, Plast. Massy 1982, 10, 22–23, CA 98(4):17092c.

K. Gehrke, Plaste and Kautschuk 1970, 251–252, CA 72(24):121951.

M. Garcia–Marti, Makromol. Chem. 1971, 144, 17–27, CA 75(6):36817.

K. Gehrke, Plaste Kaut. 1971, 18, 87–89, CA 74(24): 126114.

*Makromol. Chem.* vol. 190, pp. 515–526 (1989) "Copolymerization of Cycloalkenes with Ethylene in Presence of Chiral Zirconocene Catalysts" by W. Kaminsky and R. Spiehl.

*Journal of Macromolecular Science: Reviews in Macromolecular Chemistry and Physics*, C29 (2 & 3), pp. 201, 303 (1989) "A Review of High Resolution Liquid $^{13}$Carbon Nuclear Magnetic Resonance Characterizations of Ethylene Based Polymers".

*Journal of Non–Newtonian Fluid Mechanics*, 36, pp. 255–263 (1990) Additional Observations on the Surface Melt Fracture Behavior of Linear Low Density Polyethylene: by R. Moynihan, D. Baird, and R. Ramanathan.

*Makromol. Chem. Rapid Commun.*, pp. 89–94 (1990) "Terpolymers of Ethylene, Propene and 1,5–Hexadiene Synthesized with Zirconocene/Methylaluminoxane" by W. Kaminsky and H. Drogemuller.

*Journal of Rheology*, 35 (4),3 (May 1991) pp. 497–520 "Wall Slip of Molten High Dnsity Polyethylene. I. Sliding Plate Rheometer Studies" by S.G. Hatzikiriakos and J. M. Dealy.

*Proceedings of the 1991 IEEE Power Engineering Society*, pp. 184–190 (Sep. 22–27, 1991), "New Specialty Linear Polymers (SLP) for Power Cables" by Monica Hendewerk and Lawrence Spenadel.

*Society of Plastic Engineers Proceedings*, Polyolefins VII International Conference, Feb. 24–27, 1991, "Structure/ Property Relationships in Exxpol™ Polymers" by C. Speed, B. Trudell, A. Mehta, and F. Stehling.

*1991 Speciality Polyolefins Conference Proceedings*, "The Marketing Challenge Created by Single Site Catalysts in Polyolefins" Sep. 24, 1991, pp. 41–45 by Michael P. Jeffries. *High Polymers*, vol. XX, "Crystalline Olefin Polymers" Part I, pp. 495–501.

*1991 Polymers, Laminations & Coatings Conference*, TAPPI Proceedings, presented in Feb., 1991, pp. 289–296, "A New Family of Linear Ethylene Polymers with Enhanced Sealing Performance" by D. Van der Sanden and R.W. Halle.

*Society of Plastics Engineers 1991 Speciality Polyolefins Conference Proceedings*, pp. 41–55, "The Marketing Challenge Created by Single Site Catalysts in Polyolefins" by M. Jefferies (Sep. 24, 1991).

*Advances in Polyolefins*, by R.B. Seymour and T. Cheng, (1987) pp. 373–380 "Crystallinity and Morphology of Ethylene/α–Olefin Copolymers" by P. Schouterden, G. Groeninckx, and H. Reynaers.

*Advances in Polyolefins*, by R.B. Seymour and T. Cheng, (1987) "New Catalysis and Process for Ethylene Polymerization" pp. 337–354, by F. Karol, B. Wagner, I. Levine, G. Goeke, and A. Noshay.

Randall, *Rev. Macromoal. Chem. Phys.*, C29 (2&3), pp. 285–297. (1989).

M. Shida et al., *Polymer Engineering Science*, vol. 17, No. 11. "Correlation of Low Density Polyethylene Rheological Measurements with Optical and Processing Properties" pp. 769–774 (1977).

John Dealy, *Rheometers for Molten Plastics*, Van Nostrand Reinhold Co., pp. 97–99, (1989).

Ramamurthy, *Journal of Rheology*, "Wall Slip in Viscous Fluids and Influence of Materials Construction" John Wiley & Sons, 30 (2), pp. 337–357, (1986).

Wild et al., *Journal of Polymer Science, Poly. Phys. Ed.*, "Determination of Branching Distributions in Polyethylene and Ethylene Copolymers" John Wiley & Sons, vol. 20, pp. 441 (1982).

John Dealy, *Rheometers for Molten Plastics*, Van Nostrand Reinhold Co., pp. 250–251, (1982).

Van der Sanden & Halle, A New Family of Linear Ethylene Polymers Provides Enhanced Sealing Performance, TAPPI, pp. 99–103 (Feb. 1992).

Lambert & Zhang, Tetrakis(pentafluorophenyl)borate: A New Anion for Silylium Cations in the Condensed Phase, J.Chem. Soc., Chem. Commun., pp. 383–394, (1993).

Lambert et al. Silyl Cations in the Solid and in Solution, Organometallics, vol. 13, pp. 2430–2443 (1994).

Pohlmann & Brinckmann, Pentafluorophenyl–Metal Chemistry II: Preparation and Characterization of Group IIIA Derivatives, Z. Naturforschg. vol. 20b, pp. 5–11 (1965).

Williams & Word, The Construction of a Polyethylene Calibration Curve for Gel Permeation Chromatography using Polystyrene Fractions, Pol. Letters, vol. 6, pp. 621–624 (1968).

Kunii & Levenspiel, *Fluidization Engineering*, 2nd Ed., pp., Butterworth–Heineman (1991).

Declaration of Jean–Francois Berthiaux submitted with attached Exhibit A (Annex 2) in support of Exxon's Motion for Summary Judgment in a court action brought by Union Carbide, Jan. 26, 1995, United States District Court, Southern District of New York, 94 Civ. 8866 (LAP).

* cited by examiner

GAS PHASE POLYMERIZATION OF OLEFINS

CROSS REFERENCE TO RELATED APPLICATIONS

This application is a Continuation of U.S. application Ser. No. 08/659,976, filed Jun. 3, 1996, now U.S. Pat. No. 6,025,448, which is a CIP of U.S. application Ser. No. 08/308,068, filed Sep. 16, 1994, now abandoned, which is a CIP of U.S. application Ser. No. 08/122,852, filed Sep. 17, 1993, now abandoned, which is a CIP of U.S. application Ser. No. 08/475,737, filed Jun. 7, 1995, now abandoned, which is a CIP of U.S. application Ser. No. 08/378,998, filed Jan. 27, 1995, now abandoned, which is a CIP of U.S. application Ser. No. 08/054,379, filed Apr. 28, 1993, now abandoned, which is a Divisional of U.S. application Ser. No. 07/776,130, filed Oct. 15, 1991, now U.S. Pat. No. 5,272,236, which is a CIP of U.S. application Ser. No. 08/510,527, filed Aug. 2, 1995, now abandoned, which is a Continuation of U.S. application Ser. No. 08/010,958, filed Jan. 29, 1993, now abandoned, which is a CIP of U.S. application Ser. No. 08/208,068, filed Mar. 8, 1994, now abandoned, which is a Continuation of U.S. application Ser. No. 07/815,716, filed Dec. 30, 1991, now abandoned, which is a CIP of U.S. application Ser. No. 08/433,785, filed May 3, 1995, now abandoned, which is a Divisional of U.S. application Ser. No. 08/208,068, filed Mar. 8, 1994, now abandoned, which is a CIP of U.S. application Ser. No. 07/545,403, filed Jul. 3, 1990, now abandoned and a CIP of U.S. application Ser. No. 08/626,303, filed Apr. 1, 1996, now U.S. Pat. No. 5,763,547.

This application is also related to U.S. application Ser. No. 547,728 filed Jul. 3, 1990, now U.S. Pat. No. 5,064,802; to U.S. application Ser. No. 07/758,654 filed Sep. 12, 1991, now U.S. Pat. No. 5,132,380; to pending U.S. application Ser. No. 67,497 filed May 26, 1993; to pending U.S. application Ser. No. 67,509, filed May 26, 1993; to pending U.S. application Ser. No. 209,689 filed Mar. 10, 1994; to pending U.S. application Ser. No. 876,268 filed May 1, 1992; to U.S. application Ser. No. 108,693 filed Dec. 1, 1992, now U.S. Pat. No. 5,453,410; to U.S. application Ser. No. 8,003 filed Jan. 21, 1993, now U.S. Pat. No. 5,374,696; to pending U.S. application Ser. No. 295,768 filed Mar. 19, 1993; to U.S. application Ser. No. 294,469 filed Aug. 23, 1994, now U.S. Pat. No. 5,494,874; and to pending U.S. application Ser. No. 498,964, filed Jul. 6, 1995. All of the preceding patents and patent applications are incorporated herein by reference.

FIELD OF THE INVENTION

This invention relates to a gas phase, fluidized bed process for producing olefin polymers, particularly ethylene polymers, having improved processability. These polymers include olefin polymers having low susceptibility to melt fracture, even under high shear stress conditions, and a narrow MWD.

BACKGROUND OF THE INVENTION

The discovery of the fluidized bed process for the production of linear olefin polymers-provided a means for producing these diverse and widely used polymers with a drastic reduction in capital investment and a dramatic reduction in energy requirements as compared to then conventional processes.

To be commercially useful in a gas phase process, such as the fluid bed processes of U.S. Pat. Nos. 3,709,853; 4,003, 712 and 4,011,382, all of which are incorporated herein by reference; Canadian Pat. No. 991,798 and Belgian Pat. No. 839,380, the catalyst employed must be a highly active catalyst. Typically, levels of productivity reach from 50,000 to 1,000,000 pounds of polymer or more per pound of primary metal in the catalyst. High productivity in the gas phase processes is desired to avoid the expense of catalyst residue removal procedures. Thus, the catalyst residue in the polymer must be small enough that it can be left in the polymer without causing any undue problems to either the resin manufacturer, or to a party fabricating articles from the resin, or to an ultimate user of such fabricated articles. Where a high activity catalyst is successfully used in such fluid bed processes, the transition metal content of the resin is on the order of $\leq 20$ parts per million (ppm) of primary metal at a productivity level of $\geq 50,000$ pounds of polymer per pound of metal. Low catalyst residue contents are also important in heterogeneous catalysts comprising chlorine containing materials such as the titanium, magnesium and/or aluminum chloride complexes used in some so-called Ziegler or Ziegler-Natta type catalysts. Use of these heterogeneous catalysts results in a polymerization reaction product which is a complex mixture of polymers, with a relatively wide distribution of molecular weights. This wide distribution of molecular weights has an effect (generally detrimental) on the physical properties of the polymeric materials, e.g. decreased tensile strength, dart impact.

The molecular weight distribution (MWD), or polydispersity, is a known variable in polymers which is described as the ratio of weight average molecular weight (Mw) to number average molecular weight (Mn) (i.e., Mw/Mn), parameters which can be determined directly, for example by gel permeation chromatography techniques. The $I_{10}/I_2$ ratio, as described in ASTM D-1238, can be an indicator of the MWD in conventional heterogeneous ethylene polymers. The $I_{10}/I_2$ ratio is also an indicator of the shear sensitivity and processibility for ethylene polymers. Low density polyethylenes (LDPE) typically have a higher $I_{10}/I_2$ ratio than linear low density polyethylenes (LLDPE) or ultra low density linear polyethylenes (ULDPE) and are easier to melt process in fabrication equipment at comparable $I_2$ values.

Ethylene polymers having a narrow MWD and homogeneous comonomer distribution are known. These polymers can be produced using "single site" catalysts, such as metallocene or vanadium catalysts. While the physical properties of these polymers are generally superior to heterogeneous polymers, they are often difficult to process with conventional melt fabrication equipment. The problems are manifested, for example, in their lack of ability to sustain a bubble in a blown film process, and by a "sag" when evaluated in blow molding processes. In addition, the melt fracture surface properties of these polymers are often unacceptable at high extrusion rates, a feature that makes them less desirable for use in equipment operating at current high speed extrusion (i.e., production) rates. Extruders often exhibit.increased power consumption due to the low shear sensitivity of these polymers.

Use of the catalyst systems described in U.S. Pat. Nos. 5,374,696 and 5,453,410, both of which are incorporated herein by reference, results in the production of unique polymers having the properties as taught in U.S. Pat. No. 5,272,236 and U.S. Pat. No. 5,278,272, which are incorporated by reference. These polymers are substantially linear olefin polymers which are characterized as having a critical shear rate at the onset of surface melt fracture of at least 50 percent greater than the critical shear rate at the onset of surface melt fracture of a linear olefin polymer having about the same $I_2$ and Mw/Mn.

There is a need for a gas phase olefin polymerization catalyst that can be used more efficiently and effectively to polymerize or copolymerize ethylene with higher alpha-olefins, e.g. alpha-olefins having 3 to 20 carbon atoms. In practice, the commercial copolymers are made using monomers having only 3 to 8 carbon atoms (i.e., propylene, 1-butene, 1-hexene, 1-octene and 4-methyl-1-pentene) because of the low rate of reactivity and incorporation of the alpha olefins with larger carbon chains and, for gas phase processes, because of the lower concentration possible in the reactor for alpha-olefins with larger carbon chains. The traditional Ziegler catalysts are not particularly efficient or effective in incorporating the higher alpha-olefin comonomers into the polymer. The rate of reaction for the ethylene monomer is much greater than the rate of reaction for the higher alpha-olefin monomers in the copolymerization reaction using traditional multi-site Ziegler catalysts. Accordingly, due to the lower reaction rate of incorporating the longer chain comonomer into the growing polymer chain, the copolymer fractions containing the higher alpha-olefin comonomers are generally the lower molecular weight fraction having limited desirable physical properties. These factors also contribute to polymer particles sticking together or agglomerating in the gas phase process.

Even in the most current olefin copolymerization systems, there is still a need for a gas phase olefin polymerization catalyst which is able to incorporate efficiently larger amounts of alpha-olefins into a copolymer chain and give a polymeric product which has a narrow molecular weight distribution and is more homogeneous with respect to comonomer distribution than otherwise would be achieved using a Ziegler catalyst under comparable conditions. The properties and advantages of linear homogeneous copolymers are described in U.S. Pat. No. 3,645,992 which is incorporated herein by reference.

Canich et al. teach in U.S. Pat. No. 5,057,475, U.S. Pat. No. 5,026,798, and U.S. Pat. No. 5,096,867, all of which are incorporated herein by reference a supported catalyst system which includes an inert support material, a Group IV B metal component and an alumoxane component for use in the production of high molecular weight polyolefins. While Canich et al. teaches the use of their catalysts under various reaction conditions, the gas phase examples of their '475 patent report polymer products having a relatively broad MWD (e.g. >2.9).

There is also a need for a gas phase process to produce more homogeneous narrow molecular weight distribution polyolefins (MWD of 1.5–2.9), that have improved processability such as provided by substantially linear olefin polymers.

SUMMARY OF THE INVENTION

A fluidized bed, gas phase process for the production of an ethylene polymer or copolymer is comprised of reacting by contacting ethylene or ethylene in combination with at least one alpha-olefin and/or diolefin in the presence of a constrained geometry catalyst under polymerization conditions thereby producing a flowable particulate ethylene polymer or copolymer solid. The continuous process is particularly suited for ethylene copolymers containing $\geq 80$ mol percent of ethylene and $\leq 20$ mol percent of one or more α-olefins, particularly $C_3$–$C_8$ α-olefins, or diolefins with a Group 4 metal-containing constrained geometry catalyst at a temperature of from about 0° C. to about 110° C. The catalyst system is a constrained geometry catalyst which comprises an activated catalyst complex and optionally, a support, e.g. polyethylene, clay, cornstarch, talc, silica or other suitable materials.

Another aspect of this invention is a process for in situ blending of polymers comprising continuously contacting, under polymerization conditions, a mixture of ethylene and at least one or more α-olefins and/or diolefins in at least two fluidized bed reactors connected in series, with a catalyst with the polymerization conditions being such that an ethylene copolymer having a higher melt index is formed in at least one reactor and an ethylene copolymer having a lower melt index is formed in at least one other reactor with the provisos that:

(a) in the reactor(s) in which the lower melt index copolymer is made:
  (1) the alpha-olefin and/or diolefin is present in a ratio of about 0.01 to about 3.5 total moles of alpha-olefin and/or diolefin per mole of ethylene; and
  (2) hydrogen, if present, is present in a ratio of greater than about 0 to about 0.3 mole of hydrogen per mole of ethylene; and
(b) in the reactor(s) in which higher melt index copolymer is made:
  (1) the alpha-olefin and/or diolefin is present in a ratio of about 0.005 to about 3.0 total moles of alpha-olefin and/or diolefin per mole of ethylene; and
  (2) hydrogen is present in a ratio of about 0.05 to about 2 moles of hydrogen per mole of ethylene; and
(c) the mixture of catalyst and ethylene homopolymer or copolymer formed in one reactor in the series is transferred to an immediately succeeding reactor in the series; and
(d) the catalyst system comprises a constrained geometry catalyst and optionally, another catalyst, and
(e) catalyst may be optionally added to each reactor in the series, provided that catalyst is added to at least the first reactor in the series.

Yet another aspect of this invention is the process for in situ blending of polymers comprising continuously contacting, under polymerization conditions, a mixture of ethylene and at least one α-olefin and/or diolefin in at least two fluidized bed reactors connected in parallel, with a catalyst with the polymerization conditions being such that an ethylene copolymer having a higher melt index is formed in at least one reactor and an ethylene copolymer having a lower melt index is formed in at least one other reactor with the provisos that:

(a) in the reactor(s) in which the lower melt index copolymer is made:
  (1) said alpha-olefin and/or diolefin is present in a ratio of about 0.01 to about 3.5 total moles of alpha-olefin and/or diolefin per mole of ethylene; and
  (2) hydrogen, if present, is present in a ratio of greater than about 0 to about 0.3 mole of hydrogen per mole of ethylene; and
(b) in the reactor(s) in which higher melt index copolymer is made:
  (1) the alpha-olefin and/or diolefin is present in a ratio of about 0.005 to about 3.0 total moles of alpha-olefin and/or diolefin per mole of ethylene; and
  (2) hydrogen is present in a ratio of about 0.05 to about 2 moles of hydrogen per mole of ethylene; and
(c) the catalyst system comprises a constrained geometry catalyst and optionally, another catalyst.

In all embodiments of the invention, the constrained geometry catalyst is used in at least one of the reactors.

An advantage of this invention is that at least one constrained geometry catalyst can be used alone or in conjunction with at least one other catalyst in reactors operated in series or parallel.

Yet another advantage is that due to the ability of supported constrained geometry catalysts to incorporate efficiently longer chain higher alpha-olefin comonomers into a polymer, the range of copolymer densities which can be made in an conventional gas phase reactor without having to condense the recycle stream is dramatically increased.

DETAILED DESCRIPTION OF THE INVENTION

The Ethylene Copolymers

Figure 1:
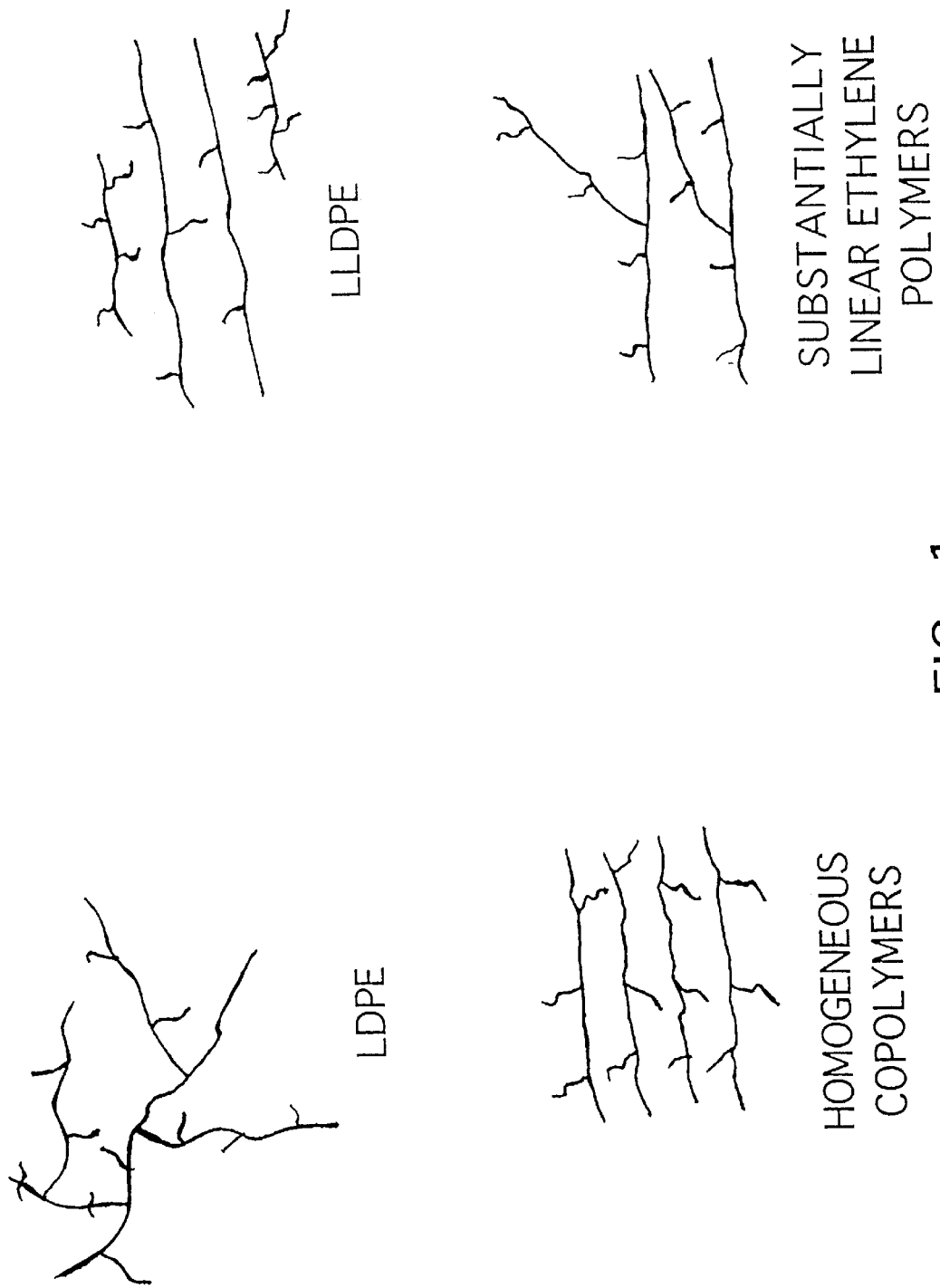
FIG. 1 graphically displays the structural characteristics of a traditional heterogeneous Ziegler polymerized LLDPE copolymer, a highly branched high pressure free radical LDPE, a homogeneously branched linear copolymer, and a substantially linear ethylene alpha olefin copolymer.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering Groups.

The copolymers which may be prepared in the process of the present invention are copolymers of a major mol percent ($\geq 80\%$) of ethylene, and a minor mol percent ($\leq 20\%$) of one or more alpha olefins or diolefins. The polymers of the present invention can be homopolymers of ethylene or they can be interpolymers of ethylene with at least one $C_3$–$C_{20}$ alpha-olefin and/or $C_4$–$C_{18}$ diolefin. The polymers of the present invention can also be interpolymers of ethylene with at least one $C_3$–$C_{20}$ alpha-olefin, $C_4$–$C_{18}$ diolefin and/or other ethylenically unsaturated monomer.

Monomers usefully polymerized according to the present invention include, for example, ethylenically unsaturated monomers, conjugated or nonconjugated dienes, polyenes, etc. Preferred monomers include the $C_2$–$C_{10}$ α-olefins especially ethylene, propene, isobutylene, 1-butene, 1-hexene, 4-methyl-1-pentene, and 1-octene, and the dienes 5-ethylidene-2-norbornene and piperylene. Other useful but less preferred monomers include styrene, halo- or alkyl substituted styrenes, tetrafluoroethylene, vinylbenzocyclobutene, 1,4-hexadiene, 1,5-hexadiene, 1,7-octadiene, 4-vinylcyclohexene, and vinylcyclohexane, 2,5-norbornadiene, 1,3-pentadiene, 1,4-pentadiene, 1,3-butadiene, isoprene and naphthenics (e.g., cyclopentene, cyclohexene and cyclooctene).

Throughout this disclosure, "melt index" or "$I_2$" is measured in accordance with ASTM D-1238 (190° C./2.16 kg); "$I_{10}$" is measured in accordance with ASTM D-1238 (190° C./10 kg). For linear polyolefins, especially linear polyethylene, it is well known that as Mw/Mn increases, $I_{10}/I_2$ also increases. With the ethylene or ethylene/α-olefin or diene substantially linear olefin polymers that can be made by this invention, the $I_{10}/I_2$ may be increased without increasing Mw/Mn. The melt index for the ethylene or ethylene/α-olefin substantially linear olefin polymers used herein is generally from about 0.01 grams/10 minutes (g/10 min) to about 1000 g/10 min, preferably from about 0.01 g/10 min to about 100 g/10 min, and especially from about 0.01 g/10 min to about 10 g/10 min.

The copolymers have a $I_{10}/I_2$ melt flow ratio of about $\geq 6$ to $\leq 18$, and preferably of about $\geq 7$ to $\leq 14$.

The whole interpolymer product samples and the individual interpolymer samples are analyzed by gel permeation chromatography (GPC) on a Waters 150 C high temperature chromatographic unit equipped with three mixed porosity bed columns (available from Polymer Laboratories), operating at a system temperature of 140 C. The solvent is 1,2,4-trichlorobenzene, from which 0.3 percent by weight solutions of the samples are prepared for injection. The flow rate is 1.0 milliliters/minute and the injection size is 200 microliters.

The molecular weight determination is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science, Polymer Letters*, Vol. 6, (621) 1968, incorporated herein by reference) to derive the following equation:

$$M_{polyethylene} = a * (M_{polystyrene})^b$$

this equation, a=0.4316 and b=1.0. Weight average molecular weight, $M_w$, is calculated in the usual manner according to the following formula: $M_w = \Sigma w_i * M_i$, where $w_i$ and $M_i$ are the weight fraction and molecular weight, respectively, of the $i^{th}$ fraction eluting from the GPC column.

The molecular weight distribution ($M_w/M_n$ or MWD) for the ethylene polymers of this invention is generally less than about 2.9, preferably less than about 2.6, more preferably less than about 2.3 and although the minimum MWD can vary to convenience, it is generally greater than about 1.5, preferably greater than about 1.7, and more preferably equal to or greater than 2.

The density of the polymers in the present invention is measured in accordance with ASTM D-792 and is generally from about 0.85 g/cm$^3$ to about 0.96 g/cm$^3$, preferably from about 0.865 g/cm$^3$ to about 0.96 g/cm$^3$. The density of the copolymer, at a given melt index level for the copolymer, is primarily regulated by the amount of the comonomer which is copolymerized with the ethylene. In the absence of the comonomer, the ethylene would homopolymerize with the catalyst of the present invention to provide homopolymers having a density of about >0.95. Thus, the addition of progressively larger amounts of the comonomers to the copolymers results up to a point in a progressive lowering of the density of the copolymer. The amount of each of the various α-olefin comonomers or dienes needed to achieve the same result will vary from monomer to monomer, under the same reaction conditions. Thus to achieve the same results, in the copolymers, in terms of a given density, at a given melt index level, larger molar amounts of the different comonomers generally would be needed in the order of $C_3 > C_4 > C_5 > C_6 > C_7 > C_8$.

The term "linear" as used herein means that the ethylene polymer does not have long chain branching. That is, the polymer chains comprising the bulk linear ethylene polymer have an absence of long chain branching, as for example the traditional linear low density polyethylene polymers or linear high density polyethylene polymers made using Ziegler polymerization processes (e.g., U.S. Pat. No. 4,076,698 (Anderson et al.)), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches. The term "linear" also refers to polymers made using uniform branching distribution polymerization processes, sometimes called homogeneous polymers, including narrow MWD (e.g. about 2) made using single site catalysts. Such uniformly branched or homogeneous polymers include those made as described in U.S. Pat. No. 3,645,992 (Elston) and those made using so-called single site catalysts in a batch reactor having relatively high ethylene concentrations (as described in U.S. Pat. No. 5,026,798 (Canich) or in U.S. Pat. No. 5,055,438 (Canich)) or those made using constrained geometry catalysts in a batch reactor also having relatively high olefin concentrations (as described in U.S. Pat. No. 5,064,802 (Stevens et al.) which is incorporated herein by reference, or in EP 0 416 815 A2 (Stevens et al.)). The uniformly branched/homogeneous polymers are those polymers in which the comonomer is randomly distributed within a given interpolymer molecule or chain, and wherein substantially all of the interpolymer molecules have the same ethylene/comonomer ratio within that interpolymer, but these polymers, too, have an absence of long chain branching, as, for example, Exxon Chemical has taught in their February 1992 Tappi Journal paper (pp 99–103).

The term "substantially linear" as used means that the bulk polymer is substituted, on average, with about 0.01 long chain branches/1000 total carbons (including both backbone and branch carbons) to about 3 long chain branches/1000 total carbons. Preferred polymers are substituted with about 0.01 long chain branches/1000 total carbons to about 1 long chain branch/1000 total carbons, more preferably from about 0.05 long chain branches/1000 total carbons to about 1 long chain branch/1000 total carbons, and especially from about 0.3 long chain branches/1000 total carbons to about 1 long chain branch/1000 total carbons.

As used herein, the term "backbone" refers to a discrete molecule, and the term "polymer" or "bulk polymer" refers in the conventional sense to the polymer as formed in a reactor. For the polymer to be a "substantially linear" polymer, the polymer must have at least enough molecules with long chain branching such that the average long chain branching in the bulk polymer is at least an average of about 0.01 long chain branches/1000 total carbons.

The term "bulk" polymer means the polymer which results from the polymerization process and, for the substantially linear polymers, includes molecules having both an absence of long chain branching, as well as molecules having long chain branching. Thus a "bulk" polymer includes all molecules formed during polymerization. For substantially linear polymers, not all molecules have long chain branching, but a sufficient amount do such that the average long chain branching content of the bulk polymer positively affects the melt rheology (i.e., the melt fracture properties).

Long chain branching (LCB) is defined herein as a chain length of at least one (1) carbon less than the number of carbons in the comonomer, whereas short chain branching (SCB) is defined herein as a chain length of the two (2) less than the number of carbons in the comonomer. For example, an ethylene/1-octene substantially linear polymer has backbones with long chain branches of at least seven (7) carbons in length, but these backbones also have short chain branches of only six (6) carbons in length, whereas an ethylene/1-hexene substantially linear polymer has long chain branches of at least five (5) carbons in length but short chain branches of only four (4) carbons in length.

Long chain branching can be distinguished from short chain branching by using $^{13}$C nuclear magnetic resonance (NMR) spectroscopy and to a limited extent, e.g. for ethylene homopolymers, it can be quantified using the method of Randall (Rev. Macromol. Chem. Phys., C29 (2&3), p. 285–297), the disclosure of which is incorporated herein by reference. However as a practical matter, current $^{13}$C nuclear magnetic resonance spectroscopy cannot determine the length of a long chain branch in excess of six (6) carbon atoms and as such, this analytical technique cannot distinguish between a seven (7) carbon branch and a seventy (70) carbon branch. The long chain branch can be as long as about the same length as the length of the polymer backbone.

U.S. Pat. No. 4,500,648, incorporated herein by reference, teaches that long chain branching frequency (LCB) can be represented by the equation LCB=$b/M_w$, wherein b is the weight average number of long chain branches per molecule and $M_w$ is the weight average molecular weight. The molecular weight averages and the long chain branching characteristics are determined by gel permeation chromatography and intrinsic viscosity methods.

The SCBDI (Short Chain Branch Distribution Index) or CDBI (Composition Distribution Branch Index) is defined as the weight percent of the polymer molecules having a comonomer content within 50 percent of the median total molar comonomer content. The CDBI of a polymer is readily calculated from data obtained from techniques known in the art, such as, for example, temperature rising elution fractionation (abbreviated herein as "TREF") as described, for example, in Wild et al, Journal of Polymer Science, Poly. Phys. Ed., Vol. 20, p. 441 (1982), or as described in U.S. Pat. Nos. 4,798,081 and 5,008,204 both of which are incorporated herein by reference. The SCBDI or CDBI for the substantially linear ethylene polymers of the present invention is typically greater than about 30 percent, preferably greater than about 50 percent, more preferably greater than about 80 percent, and most preferably greater than about 90 percent.

"Melt tension" is measured by a specially designed pulley transducer in conjunction with the melt indexer. Melt tension is the load that the extrudate or filament exerts while passing over the pulley onto a two inch drum that is rotating at the standard speed of 30 rpm. The melt tension measurement is similar to the "Melt Tension Tester" made by Toyoseiki and is described by John Dealy in "Rheometers for Molten Plastics", published by Van Nostrand Reinhold Co. (1982) on page 250–251. The melt tension of the substantially linear polymers of this invention is also surprisingly good, e.g., as high as about 2 grams or more. For the substantially linear ethylene interpolymers of this invention, especially those having a very narrow molecular weight distribution (i.e., $M_w/M_n$ from 1.5 to 2.9), the melt tension is typically at least about 5 percent, and can be as much as about 60 percent, greater than the melt tension of a conventional linear ethylene interpolymer having a melt index, polydispersity and density each within ten percent of the substantially linear ethylene polymer.

A unique characteristic of the substantially linear polymer is a highly unexpected flow property where the $I_{10}/I_2$ value is essentially independent of polydispersity index (i.e., $M_w/M_n$). This is contrasted with conventional Ziegler polymerized heterogeneous polyethylene resins and with conventional single site catalyst polymerized homogeneous polyethylene resins having rheological properties such that as the polydispersity index increases, the $I_{10}/I_2$ value also increases.

Processing Index Determination

The "rheological processing index" (PI) is the apparent viscosity (in kpoise) of a polymer and is measured by a gas extrusion rheometer (GER). The GER is described by M. Shida, R. N. Shroff and L. V. Cancio in Polym. Eng. Sci., Vol. 17, no. 11, p. 770 (1977), and in "Rheometers for Molten Plastics" by John Dealy, published by Van Nostrand Reinhold Co. (1982) on page 97–99. The processing index is measured at a temperature of 190 C, at nitrogen pressure of 2500 psig using a 0.0296 inch (752 micrometers) diameter (preferably 0.0143 inch diameter die for high flow polymers, e.g. 50–100 melt index or greater), 20:1 L/D die having an entrance angle of 180 degrees. The GER processing index is calculated in millipoise units from the following equation:

$$PI = 2.15 \times 10^6 \text{ dyne/cm}^2/(1000 \times \text{shear rate}),$$

where: $2.15 \times 10^6$ dyne/cm$^2$ is the shear stress at 2500 psi, and the shear rate is the shear rate at the wall as represented by the following equation:

$$32 \, Q'/(60 \text{ sec/min})(0.745)(\text{Diameter} \times 2.54 \text{ cm/in})^3, \text{ where:}$$

Q' is the extrusion rate (g/min),
0.745 is the melt density of polyethylene (g/cm$^3$), and
Diameter is the orifice diameter of the capillary (inches).

The PI is the apparent viscosity of a material measured at apparent shear stress of $2.15 \times 10^6$ dyne/cm$^2$.

For the substantially linear ethylene polymers (or ethylene/alpha-olefin copolymers or interpolymers) produced by this invention, the PI is less than or equal to 70 percent of that of a conventional linear ethylene polymer (or ethylene/alpha-olefin copolymer or interpolymer) having an $I_2$, $M_w/M_n$ and density each within ten percent of the substantially linear ethylene polymer.

An apparent shear stress vs. apparent shear rate plot is used to identify the melt fracture phenomena over a range of nitrogen pressures from 5250 to 500 psig using the die or GER test apparatus previously described. According to Ramamurthy in Journal of Rheology, 30(2), 337–357, 1986, above a certain critical flow rate, the observed-extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture is characterized at the beginning of losing extrudate gloss at which the surface roughness of extrudate can only be detected by 40×magnification. The critical shear rate at onset of surface melt fracture for the substantially linear ethylene polymers is at least 50 percent greater than the critical shear rate at the onset of surface melt fracture of a linear ethylene polymer having an $I_2$, $M_w/M_n$ and density each within ten percent of the substantially linear ethylene polymer. Preferably the critical shear stress at onset of surface melt fracture for the substantially linear ethylene polymers of the invention is greater than about $2.8 \times 10^6$ dyne/cm$^2$.

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and critical shear stress at onset of gross melt fracture (OGMF) are based on the changes of surface roughness and configurations of the extrudates extruded by a GER. For the substantially linear ethylene polymers of the invention, the critical shear stress at onset of gross melt fracture is preferably greater than about $4 \times 10^6$ dyne/cm$^2$.

For the processing index and melt fracture tests, the ethylene polymers and substantially linear ethylene copolymers contain antioxidants such as phenols, hindered phenols, phosphites or phosphonites, preferably a combination of a phenol or hindered phenol and a phosphite or a phosphonite.

Suitable catalysts for use herein comprise constrained geometry complexes in combination with an activating cocatalyst or activating technique. Examples of such constrained geometry complexes, methods for their preparation and for their activation are disclosed in U.S. application Ser. No. 07/401,344, filed Aug. 31, 1989 (abandoned), U.S. application Ser. No. 545,403, filed Jul. 3, 1990 (EP-A416, 815); U.S. application Ser. No. 547,718, filed Jul. 3, 1990 (EP-A468,651); U.S. application Ser. No. 702,475, filed May 20, 1991 (EP-A-514,828); U.S. application Ser. No. 876,268, filed May 1, 1992, (EP-A-520,732) and U.S. application Ser. No. 08/008,003, filed Jan. 21, 1993, as well as U.S. Pat. Nos.: 5,055,438, 5,057,475, 5,096,867, 5,064,802 and 5,132,380, of which all U.S. Patents and Patent Applications are incorporated herein by reference.

Suitable metal complexes for use herein correspond to the formula:

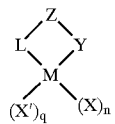

or dimers thereof,
wherein:
M is a Group 4 metal in the +2,+3 or +4 formal oxidation state, preferably M is titanium, zirconium or hafnium, most preferably titanium;
L is a group containing a cyclic, delocalized, aromatic, anionic, Π bonded system through which the L group is bound to M, and which L group is also bound to Z, said L group containing up to 60 nonhydrogen atoms;
Z is a moiety covalently bound to both L and Y, comprising boron, or a member of Group 14 of the Periodic Table of the Elements, said moiety having up to 60 non-hydrogen atoms;
Y is a moiety comprising nitrogen, phosphorus, sulfur or oxygen through which Y is covalently bound to both Z and M, said moiety having up to 25 nonhydrogen atoms;
X' independently each occurrence is a neutral Lewis base containing up to 40 nonhydrogen atoms;
X independently each occurrence is a monovalent anionic moiety having up to 20 non-hydrogen atoms, provided however that neither X is an aromatic group that is Π-bonded to M, optionally, two X groups may be covalently bound together forming a divalent dianionic moiety having both valences bound to M, or further optionally one or more X and one X' group may be bonded together thereby forming a moiety that is both covalently bound to M and coordinated thereto by means of Lewis base functionality;
q is a number from 0 to 1; and
is 0, 1 or 2 depending on the formal oxidation state of M Suitable complexes for use herein include: 1-(tert-butylamido)-2-(tetramethyl-η$^5$-cyclopentadienyl) ethanediyltitanium dimethyl, 1-(tert-butylamido)-2-

(tetramethyl-η⁵-cyclopentadienyl)ethanediyltitanium dibenzyl, tert-butylamido(tetramethyl-η⁵-cyclopentadienyl) dimethylsilanetitanium dimethyl, tert-butylamido (tetramethyl-η⁵-cyclopentadienyl)dimethylsilanetitanium dibenzyl, (methylamido)(tetramethyl-η⁵-cyclopentadienyl) dimethylsilanetitanium dimethyl, (methylamido) (tetramethyl-η⁵-cyclopentadienyl)dimethylsilanetitanium dibenzyl, (phenylamido)(tetramethyl-η⁵-cyclopentadienyl) dimethylsilanetitanium dimethyl, (phenylamido) (tetramethyl-η⁵-cyclopentadienyl)dimethylsilanetitanium dibenzyl, (benzylamido)(tetramethyl-η⁵-cyclopentadienyl) dimethylsilanetitanium dimethyl, (benzylamido) (tetramethyl-η⁵-cyclopentadienyl)dimethylsilanetitanium dibenzyl, (tert-butylamido)(η⁵-cyclopentadienyl)-1,2-ethanediyltitanium dimethyl, (tert-butylamido)(η⁵-cyclopentadienyl)-1,2-ethanediyltitanium dibenzyl, (tert-butylamido)(η⁵-cyclopentadienyl)dimethylsilanetitanium dimethyl, (tert-butylamido)(η⁵-cyclopentadienyl) dimethylsilanetitanium dibenzyl, (methylamido) (η⁵-cyclopentadienyl)dimethylsilanetitanium dimethyl, (t-butylamido)(tetramethyl-η⁵-cyclopentadienyl) dimethylsilanetitanium (II) 1,4-diphenyl-1,3-butadiene, (t-butylamido)indenyldimethylsilanetitanium dimethyl, (t-butylamido)indenyldimethylsilanetitanium dibenzyl, (benzylamido)indenyldimethylsilanetitanium dibenzyl, (t-butylamido)(tetramethyl-η⁵-cyclopentadienyl) dimethylsilanetitanium (IV) allyl, (t-butylamido) (tetramethyl-η⁵-cyclopentadienyl)dimethylsilanetitanium (III) 2,4-dimethylpentadienyl, (t-cyclododecylamido) (tetramethyl-η⁵-cyclopentadienyl)dimethylsilanetitanium (III) 2-(N,N-dimethylamino)benzyl, (t-butylamido) (tetramethyl-η⁵-cyclopentadienyl)dimethylsilanetitanium (III) 2-(N,N-dimethylamino)benzyl, 1-(t-butylamido)-2-(tetramethyl-η⁵-cyclopentadienyl)ethanediyltitanium (III) 2-(N,N-dimethylamino)benzyl 1-(t-butylamido)-2-(η⁵-indenyl)ethanediyltitanium dimethyl, 1-(t-butylamido)-2-(η⁵-indenyl)ethanediyltitanium dibenzyl, (t-butylamido) (η⁵-tetrahydroindenyl)dimethylsilanetitanium dimethyl, (t-butylamido)(η⁵-tetrahydroindenyl) dimethylsilanetitanium diphenyl, 1-(t-butylamido)-2-(η⁵-tetrahydroindenyl)ethanediyltitanium dimethyl, 1-(t-butylamido)-2-(η⁵-tetrahydroindenyl)ethanediyltitanium dibenzyl, (t-butylamido)(η⁵-fluorenyl) dimethylsilanetitanium dimethyl, (t-butylamido)(η⁵-fluorenyl)dimethylsilanetitanium dibenzyl, 1-(t-butylamido)-2-(η⁵-fluorenyl)ethanediyltitanium dimethyl, 1-(t-butylamido)-2-(η⁵-fluorenyl)ethanediyltitanium dibenzyl, (t-butylamido)(η⁵-tetrahydrofluorenyl) dimethylsilanetitanium dimethyl, (t-butylamido)(η⁵-tetrahydrofluorenyl)dimethylsilanetitanium dibenzyl, 1-(t-butylamido)-2-(η⁵-tetrahydrofluorenyl)ethanediyltitanium dimethyl, 1-(t-butylamido)-2-(η⁵-tetrahydrofluorenyl) ethanediyltitanium dibenzyl (t-butylamido)(η⁵-octahydrofluorenyl)dimethylsilanetitanium dimethyl (t-butylamido)(η⁵-octahydrofluorenyl) dimethylsilanetitanium dibenzyl, 1-(t-butylamido)-2-(η⁵-octahydrofluorenyl)ethanediyltitanium dimethyl, 1-(t-butylamido)-2-(η⁵-octahydrofluorenyl)ethanediyltitanium dibenzyl, and the corresponding zirconium or hafnium coordination complexes.

The skilled artisan will recognize that additional members of the foregoing list will include the corresponding zirconium or hafnium containing derivatives, as well as complexes that are variously substituted as herein defined.

In one embodiment of this invention, the complexes can be prepared by contacting a precursor Group 4 metal compound containing 2 displaceable ligand groups with a source of a dianionic ligand, (L-Z-Y)²⁻, and optionally, if the precursor compound is in a lower formal oxidation state than the desired complex, oxidizing the resulting complex, or if the precursor compound is in a higher formal oxidation state than the desired complex, reducing the resulting complex.

Further according to the present invention there is provided a catalyst system useful for polymerization of addition polymerizable monomers comprising:

A) 1) one or more of the above metal complexes or the reaction product of the above described process, and
2) one or more activating cocatalysts;

or

B) the reaction product formed by converting one or more of the above metal complexes or the reaction product of the above described process to an active catalyst by use of an activating technique.

By the term "divalent derivatives" is meant that L is bonded to both Z and M. Suitable inert substituents on L include hydrogen, hydrocarbyl, halocarbyl, halohydrocarbyl, silyl, germyl, halo, amino, phosphino, cyano, hydrocarbyloxy, siloxy and combinations thereof, each of said inert substituents having up to 20 nonhydrogen atoms, or optionally, two or more such substituents (except hydrogen, cyano or halo) together form a ring structure, particularly a fused ring structure. Desirably, such L groups contain up to 50 non-hydrogen atoms. Cyclopentadienyl, indenyl, fluorenyl, tetrahydroindenyl, tetrahydrofluorenyl, and octahydrofluorenyl and the foregoing inertly substituted derivatives thereof are specifically included within the above definition of L groups.

Preferred examples of X groups include: hydrocarbyl, carboxylate, sulfonate, hydrocarbyloxy, siloxy, amido, phosphido, sulfido, and silyl groups; as well as halo-, amino-, hydrocarbyloxy-, siloxy-, silyl-, and phosphino-substituted derivatives of such hydrocarbyl, carboxylate, sulfonate, hydrocarbyloxy, siloxy, amido, phosphido, sulfido, or silyl groups; hydride, halide and cyanide, said X group having up to 20 nonhydrogen atoms; or alternatively, two X groups together are a hydrocarbadiyl, or a substituted hydrocarbadiyl group wherein the substituent is independently each occurrence a hydrocarbyl or silyl group of up to 20 nonhydrogen atoms, said group forming a metallacycle, preferably a metallacyclopentene, with M.

More preferred X groups are hydride, hydrocarbyl (including cyclohydrocarbyl), hydrocarbyloxy, amido, silyl, silylhydrocarbyl, siloxy, halide and aminobenzyl. Especially suited are hydride, chloride, methyl, neopentyl, benzyl, phenyl, dimethylamido, 2-(N,N-dimethylamino)benzyl, allyl, methyl-substituted allyl (all isomers), pentadienyl, 2-methylpentadienyl, 3-methylpentadienyl, 2,4-dimethylpentadienyl, 6,6-dimethylcyclohexadienyl, and tri-methylsilylmethyl. More preferred of two X groups together are 2-butene-1,4-diyl, 2,3-dimethyl-1,4-diyl, 2-methyl-2-butene-1,4-diyl, butane-1,4-diyl, propane-1,3-diyl, pentane-1,5-diyl, and 2-pentene-1,5-diyl.

Preferred X' groups include phosphines, phosphites, ethers, amines, salts of Group 1 or 2 metals, $C_{5-40}$ neutral conjugated dienes and mixtures of the foregoing X' groups. Examples of the foregoing especially include trimethylphosphine, triethylphosphine, trifluorophosphine, triphenylphosphine, bis-1,2-(dimethylphosphino)ethane, trimethylphosphite, triethylphosphite, dimethylphenylphosphite, tetrahydrofuran, diethyl ether, carbon monoxide, pyridine, bipyridine, tetramethylethylene-diamine (TMEDA), dimethoxyethane (DME), dioxane, triethylamine, lithium chloride, magnesium chloride, 1,4-diphenyl-1,3-butadiene and 1,3-pentadiene.

13

Further preferred metal coordination complexes used according to the present invention correspond to the formula:

$$\begin{array}{c} Z\text{---}Y \\ / \phantom{M} / \\ Cp\text{---}M\text{---}(X)_n \\ \phantom{Cp\text{---}M}\backslash \\ \phantom{Cp\text{---}M}(X')_q \end{array}$$

wherein Z, M, Y, X, X', q and n are as previously defined; and

Cp is a $C_5H_4$ group bound to Z and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, two such substituents (except cyano or halo) together cause Cp to have a fused ring structure.

More preferred metal coordination complexes used according to the present invention correspond to the formula:

wherein:

R' each occurrence is independently selected from hydrogen, hydrocarbyl silyl, and combinations thereof, said R' having up to 20 nonhydrogen atoms, and optionally, two R' groups (where R' is not hydrogen) together form a divalent derivative thereof connected to adjacent positions of the cyclopentadienyl ring to form a fused ring structure:

Y is —O—, —S—, —NR*—, —PR*—;

Z is SiR*2, CR*2, SiR*2SiR*2, CR*₂CR*2, CR*=CR*, or CR*2SiR*2; wherein:

R* each occurrence is independently hydrogen, or a member selected from hydrocarbyl, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system.

M is titanium, hafnium or zirconium in the +2, +3 or +4 formal oxidation state; and X is chloro, hydrocarbyl, hydrocarbyloxy, silyl or N,N-dialkylamino substituted hydrocarbyl group;

X' is 1,4-diphenylbutadiene, 1,3-pentadiene, or 2,4-hexadiene;

q is 0 or 1; and n is 0, 1 or 2.

Preferably, R' independently each occurrence is hydrogen, alkyl, silyl, halo and combinations thereof said R' having up to 10 nonhydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen or halo) are linked together, the entire $C_5R'_4$ group thereby being, for examply, an indenyl, tetrahydroindenyl, fluorenyl, tetrahydrofluorenyl, or octahydrofluorenyl group.

14

Further, preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-12}$ hydrocarbyl.

Most highly preferred metal coordination complexes are amidosilane- or amidoalkanediyl- compounds corresponding to the formula:

wherein:

R' is independently each occurrence selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of cyclopentadienyl ring;

E is independently each occurrence silicon or carbon.

R'" is independently each occurrence hydrogen or $C_{1-10}$ hydrocarbyl;

R" is hydrocarbyl or silyl, especially an aryl, benzyl, hydrocarbyl substituted aryl, hydrocarbyl substituted benzyl, secondary or tertiary alkyl or tertiary silyl group of up to 12 nonhydrogen atoms;

M is titanium in the +2, +3 or +4 formal oxidation state;

m is 1 to 2;

n is 0, 1 or 2;

q is 0 or 1;

X is methyl, allyl, phenyl, benzyl, chloro, 2-(N,N-dimethylamino)benzyl or trimethylsilylmethyl; and X' is 1,4-diphenyl-1,3-butadiene or 1,3-pentadiene.

Examples of the metal complexes used according to the present invention include compounds wherein R" is methyl, ethyl, propyl, butyl, pentyl, hexyl (including all isomers of the foregoing where applicable), cyclododecyl, norbornyl, benzyl, or phenyl; $(ER'''_2)_m$ is dimethylsilyl, or ethanediyl; and the cyclic delocalized aromatic, anionic Π-bonded group is cyclopentadienyl, tetramethylcyclopentadienyl, indenyl, tetrahydroindenyl, fluorenyl, tetrahydrofluorenyl or octahydrofluorenyl.

Most highly preferred metal complexes used according to the present invention are (1-tert-butylamido)-2-(tetramethyl-$\eta^5$-cyclopentadienyl)ethanediyltitanium dimethyl, 1-(tert-butylamido)-2-(tetramethyl-$\eta^5$-cyclopentadienyl)ethanediyltitanium dibenzyl, (tert-butylamido)(tetramethyl-$\eta^5$-cyclopentadienyl) dimethylsilanetitanium dimethyl, (tert-butylamido)(tetramethyl-$\eta^5$cyclopentadienyl)dimethylsilanetitanium dibenzyl, (t-butylamido)(tetramethyl-$\eta^5$-cyclopentadienyl) dimethylsilanetitanium (II) 1,4-diphenyl-1,3-butadiene,(t-butylamido)(tetramethyl-$\eta^5$-cyclopentadienyl) dimethylsilanetitanium (II), 1,3-pentadiene, 1-(t-butylamido)-2-(tetramethyl-$\eta^5$-cyclopentadienyl) ethanediyltitanium (II), 1,4-diphenyl-1,3-butadiene (t-butylamido)($\eta^5$-tetrahydroindenyl) dimethylsilanetitanium dimethyl, (t-butylamido)($\eta^5$- tetrahydroindenyl)dimethylsilanetitanium diphenyl, 1-(t-butylamido)-2-($\eta^5$-tetrahydroindenyl)ethanediyltitanium dimethyl, (t-butylamido)($\eta^5$-tetrahydrofluorenyl) dimethylsilanetitanium dimethyl, (t-butylamido)($\eta^5$-tetrahydrofluorenyl)dimethylsilanetitanium dibenzyl, 1-(t-butylamido)-2-($\eta^5$-tetrahydrofluorenyl)ethanediyltitanium dimethyl, 1-(t-butylamido)-2-($\eta^5$-tetrahydrofluorenyl) ethanediyltitanium dibenzyl (t-butylamido)($\eta^5$-octahydrofluorenyl)dimethylsilanetitanium dimethyl (t-butylamido)($\eta^5$-octahydrofluorenyl) dimethylsilanetitanium dibenzyl, 1-(t-butylamido)-2-($\eta^5$-octahydrofluorenyl)ethanediyltitanium dimethyl, 1-(t-butylamido)-2-($\eta^5$-octahydrofluorenyl)ethanediyltitanium dibenzyl.

The metal complexes used in this invention are rendered catalytically active by combination with an activating cocatalyst or by use of an activating technique. Suitable activating cocatalysts for use herein include neutral Lewis acids such as alumoxane (modified and unmodified), $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. No. 5,153,157 and U.S. Pat. No. 5,064,802 both of which are hereby incorporated by reference, EP-A-277,003, EP-A-468,651 (equivalent to U.S. Ser. No. 07/547,718), EP-A-520,732 (equivalent to U.S. Ser. No. 07/876,268), and EP-A-520,732 (equivalent to U.S. Ser. No. 07/884,966 filed May 1, 1992).

The alumoxane used as an activating cocatalyst in this invention is of the formula $(R^4_x(CH_3)_yAlO)_p$, in which $R^4$ is a linear, branched or cyclic $C_1$ to $C_6$ hydrocarbyl, x is from 0 to about 1, y is from about 1 to 0, and p is an integer from about 3 to about 25, inclusive. The preferred alumoxane components, referred to as modified methylalumoxanes, are those wherein $R^4$ is a linear, branched or cyclic $C_3$ to $C_9$ hydrocarbyl, x is from about 0.15 to about 0.50, y is from about 9.85 to about 0.5 and p is an integer between 4 and 20, inclusive; still more preferably, $R^4$ is isobutyl, tertiary butyl or n-octyl, x is from about 0.2 to about 0.4, y is from about 0.8 to about 0.6 and p is an integer between 4 and 15, inclusive. Mixtures of the above alumoxanes may also be employed in the practice of the invention.

Most preferably, the alumoxane is of the formula $(R^4_x(CH_3)_yAlO)_p$, wherein $R^4$ is isobutyl or tertiary butyl, x is about 0.25, y is about 0.75 and p is from about 6 to about 8.

Particularly preferred alumoxanes are so-called modified alumoxanes, preferably modified methylalumoxanes (MMAO), that are completely soluble in alkane solvents, for example heptane, and include very little, if any, trialkylaluminum. A technique for preparing such modified alumoxanes is disclosed in U.S. Pat. No. 5,041,584 (which is incorporated by reference). Alumoxanes useful as an activating cocatalyst in this invention may also be made as disclosed in U.S. Pat. Nos. 4,542,199; 4,544,762; 4,960,878; 5,015,749; 5,041,583 and 5,041,585 (all of which are incorporated by reference).

Combinations of neutral Lewis acids, especially the combination of a trialkyl aluminum compound having from 1 to 4 carbons in each alkyl group and a halogenated tri (hydrocarbyl)boron compound having from 1 to 10 carbons in each hydrocarbyl group, especially tris (pentafluorophenyl)borane, and combinations of neutral Lewis acids, especially tris(pentafluorophenyl)borane, with nonpolymeric, compatible noncoordinating ion-forming compounds are also useful activating cocatalysts.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

In one embodiment of this invention, the activating cocatalysts may be represented by the following general formula:

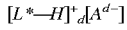

wherein:

L* is a neutral Lewis base;

[L*—H]⁺ is a Bronsted acid;

$A^{d-}$ is a noncoordinating, compatible anion having a charge of d⁻, and d is an integer from 1 to 3.

More preferably $A^{d-}$ corresponds to the formula: $[M'^{k+} Q_{n'}]^{d-}$ wherein:

k is an integer from 1 to 3;

n' is an integer from 2 to 6;

n'−k=d;

M' is an element selected from Group 13 of the Periodic Table of the Elements; and Q independently each occurrence is selected from hydride, dialkylamido, halide, hydrocarbyl, hydrocarbyloxy, halosubstituted-hydrocarbyl, halosubstituted hydrocarbyloxy, and halo substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, which is incorporated by reference.

In a more preferred embodiment, d is one, i.e., the counter ion has a single negative charge and is $A^-$. Activating cocatalysts comprising boron which are particularly useful in the preparation of catalysts of this invention may be represented by the following general formula: $[L^*—H]^+$ $[BQ_4]^-$ wherein:

$[L^*—H]^+$ is as previously defined;

B is boron in an oxidation state of 3; and

Q is a hydrocarbyl-, hydrocarbyloxy-, fluorinated hydrocarbyl-, fluorinated hydrocarbyloxy-, (hydrocarbyl substituted silyl), or fluoro-substituted hydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Illustrative, but not limiting, examples of boron compounds which may be used as an activating cocatalyst in the preparation of the catalysts of this invention are tri-substituted ammonium salts such as: trimethylammonium tetraphenylborate, triethylammonium tetraphenylborate, tripropylammonium tetraphenylborate, tri(n-butyl) ammonium tetraphenylborate, tri(t-butyl)ammonium tetraphenylborate, N,N-dimethylanilinium tetraphenylborate, N,N-diethylanilinium tetraphenylborate, N,N-dimethyl-2,4,6-trimethylanilinium tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri (sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris (pentafluorophenyl) borate, N,N-dimethylanilinium tetrakis (4-(trimethylsilyl)-2, 3, 5, 6-tetrafluorophenyl) borate, N,N-dimethylanilinium tetrakis(4-(triisopropylsilyl)-2, 3, 5, 6-tetrafluorophenyl) borate, N,N-dimethylanilinium pentafluorophenoxytris(pentafluorophenyl) borate, N,N-diethylanilinium tetrakis(pentafluorophenyl) borate, N,N-dimethyl-2,4,6-trimethylanilinium tetrakis (pentafluorophenyl) borate, trimethylammonium tetrakis(2, 3,4,6-tetrafluorophenyl)borate, triethylammonium tetrakis (2,3,4,6-tetrafluorophenyl) borate, tripropylammonium tetrakis(2,3,4,6-tetrafluorophenyl) borate, tri(n-butyl) ammonium tetrakis(2,3,4,6-tetrafluorophenyl) borate, dimethyl(t-butyl)ammonium tetrakis(2,3,4,6-tetrafluorophenyl) borate, N,N-dimethylanilinium tetrakis (2,3,4,6tetrafluorophenyl) borate, N,N-diethylanilinium tetrakis(2,3,4,6-tetrafluorophenyl) borate, and N,N-dimethyl-2,4,6-trimethylanilinium tetrakis(2,3,4,6-tetrafluorophenyl) borate;

dialkyl ammonium salts such as:
di-(i-propyl)ammonium tetrakis(pentafluorophenyl) borate, and
dicyclohexylammonium tetrakis(pentafluorophenyl) borate;

tri-substituted phosphonium salts such as:
triphenylphosphonium tetrakis(pentafluorophenyl) borate,
tri(o-tolyl)phosphonium tetrakis(pentafluorophenyl) borate, and
tri(2,6-dimethylphenyl)phosphonium tetrakis (pentafluorophenyl) borate;

di-substituted oxonium salts such as:
diphenyloxonium tetrakis(pentafluorophenyl) borate,
di(o-tolyl)oxonium tetrakis(pentafluorophenyl) borate, and
di(2,6-dimethylphenyl)oxonium tetrakis (pentafluorophenyl) borate;

di-substituted sulfonium salts such as:
diphenylsulfonium tetrakis(pentafluorophenyl) borate,
di(o-tolyl)sulfonium tetrakis(pentafluorophenyl) borate, and
di(2,6-dimethylphenyl)sulfonium tetrakis (pentafluorophenyl) borate.

Preferred $[L^*—H]^+$ cations are N,N-dimethylanilinium and tributylammonium.

Another suitable ion forming, activating cocatalyst comprises a salt of a cationic oxidizing agent and a noncoordinating, compatible anion represented by the formula:

$$(ox^{e+})_d(A^{d-})_e$$

wherein:

$Ox^{e+}$ is a cationic oxidizing agent having a charge of $e^+$;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$ĉ^+A^-$$

wherein:

$ĉ^+$ is a $C_{1-20}$ carbenium ion; and $A^-$ is as previously defined. A preferred carbenium ion is the trityl cation, i.e., triphenylmethylium.

A further suitable ion forming, activating cocatalyst comprises a compound which is a salt of a silylium ion and a noncoordinating, compatible anion represented by the formula:

$$R_3Si(X')_q^+A^-$$

wherein:

R is $C_{1-10}$ hydrocarbyl, and X', q and $A^-$ are as previously defined.

Preferred silylium salt activating cocatalysts are trimethylsilylium tetrakis(pentafluorophenyl)borate, triethylsilylium(tetrakispentafluoro)phenylborate and ether substituted adducts thereof. Silylium salts have been previously generically disclosed in *J. Chem Soc. Chem.Comm.*, 1993, 383–384, as well as Lambert, J. B., et al., *Organometallics*, 1994, 13, 2430–2443.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, which is incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100 C), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra-n-butylammonium- and tetraethylammonium- cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra-n-butylammonium tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in U.S. patent application Ser. No. 08/304,314 filed Sep. 12, 1994.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group. molar ratio of catalyst/cocatalyst employed preferably ranges from 1:10,000 to 100:1, more preferably from 1:5000 to 10:1, most preferably from 1:100 to 1:1. In one embodiment of the invention the cocatalyst can be used in combination with a tri(hydrocarbyl)aluminum compound having from 1 to 10 carbons in each hydrocarbyl group. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 1 to 6 carbons in each alkyl group, especially those wherein the alkyl groups are methyl, ethyl, propyl, isopropyl, n-butyl, isobutyl, pentyl, neopentyl or isopentyl. The molar ratio of metal complex to aluminum compound is preferably from 1:10,000 to 100:1, more preferably from 1:1000 to 10:1, most preferably from 1:500 to 1:1. A most preferred borane activating cocatalyst comprises a strong Lewis acid, especially tris (pentafluorophenyl)borane.

Other catalysts which are useful as the catalyst compositions of this invention, especially compounds containing other Group 4 metals, will, of course, be apparent to those skilled in the art.

Description of a Continuous Polymerization

The Polymerization Reaction

The polymerization reaction is conducted by contacting a gaseous stream of the monomers, in a gas phase process, such as in the fluid bed process described below, and substantially in the absence of catalyst poisons such as moisture, oxygen, CO and $CO_2$, with a catalytically effective amount of the activated catalyst composition at a temperature and pressure sufficient to initiate the polymerization reaction.

In order to achieve the desired density ranges in the polymers it is necessary to copolymerize enough of the comonomers with ethylene to achieve a level of up to 20 mol percent of the comonomer in the copolymer. The amount of comonomer needed to achieve this result will depend on the particular comonomer(s) employed.

Typically the various comonomers that are copolymerized with ethylene in order to provide polymers having the desired density range at any given melt index range from 0 to 20 mol percent in the copolymer. The relative molar concentration of such comonomers to ethylene ($C_x/C_2$), which are present under reaction equilibrium conditions in the reactor will vary depending on the choice of comonomer and the desired copolymer density.

A fluidized bed reaction system which can be used in the practice of the process of the present invention is taught in U.S. Pat. No. 4,543,399 which is incorporated by reference. A typical fluidized bed reactor can be described as follows:

The bed is usually made up of the same granular resin that is to be produced in the reactor. Thus, during the course of the polymerization, the bed comprises formed polymer particles, growing polymer particles, and catalyst particles fluidized by polymerization and modifying gaseous components pass upward through the bed at a flow rate or velocity sufficient to cause the particles to remain separated with the bed exhibiting fluid-like behavior. The fluidizing gas comprises the initial gaseous feed of monomers, make-up feed, and cycle (recycle) gas, i.e., comonomers, hydrogen and, if desired; an inert carrier gas. Examples of such inert carrier gases include nitrogen, methane, ethane or propane, which are inert with respect to the polymerization reaction.

The essential parts of the reaction system are the polymerization reaction vessel, catalyst injection system, the fluidized bed, the gas distribution plate, inlet and outlet piping, a compressor, cycle gas cooler, and a product discharge system. In the vessel, there is a reaction zone which contains the bed and a velocity reduction zone which is above the reaction zone. Both are above the gas distribution plate. Advantages of the product of subject process are the homogeneity and uniformity of the physical properties throughout the resulting polymer and the high strength and toughness obtained without processing difficulty.

It will be apparent to the skilled artisan that use of a supported constrained geometry catalyst increases the range of reactor conditions that may be used before condensing components in the recycle stream. But if one chooses to condense components in the recycle stream, then it may be desirable in some instances to raise the dew point temperature of the recycle stream to further increase heat removal as taught in U.S. Pat. Nos. 4,543,339 and 4,588,790 which are incorporated by reference. The recycle stream dew point temperature can be increased by: (1) raising the operating pressure of the reaction system; (2) increasing the concentrations of inert condensable compounds in the reaction system; and/or (3) reducing the concentration of inert non-condensable compounds in the reaction system. In one embodiment of this invention, the dew point temperature of the recycle stream may be increased by the addition of a condensable fluid to the recycle stream which is inert to the catalyst, reactants, and the products of the polymerization reaction. The fluid can be introduced into the recycle stream with the make-up fluid or by any other means or at any other point in the system. Examples of such fluids are saturated hydrocarbons, such as butanes, pentanes or hexanes.

A primary limitation on the extent to which the recycle gas stream can be cooled below the dew point is in the requirement that the gas-to-liquid ratio be maintained at a level sufficient to keep the liquid phase of the two-phase recycle mixture in an entrained or suspended condition until the liquid is vaporized. It is also necessary for sufficient velocity of the upwardly flowing fluid stream in the reaction zone to maintain fluidization of the bed. This limitation can be overcome by collecting the condensed phase and introducing it to the fluidized bed separately from the recycled gaseous stream.

Multiple reactor polymerization processes are also useful in the present invention, such as those disclosed in U.S. Pat. Nos. 3,914,342, 5,047,468, 5,126,398 and 5,149,738, all of which are incorporated herein by reference. The multiple reactors can be operated in series or in parallel, with at least one constrained geometry catalyst employed in at least one of the reactors.

In this aspect of this invention resins are manufactured and blended in situ. Multiple reactor polymerization processes may be used to produce in-situ blended polymers with enhanced physical properties and/or processability. In-situ blends of different molecular weights and/or different densities may be produced for specific and desired physical and/or processability requirements. For example, two reactors can be used in series to produce resins with a bimodal molecular weight distribution. In another example, two reactors could produce resins with a bimodality in density or short chain branching. More than two reactors in series can be used to make more molecular weight or density components for in-situ blends. Each reactor separately can have a constrained geometry catalyst or a conventional Ziegler-Natta catalyst as needed for obtaining the in-situ blended polymer with the desired properties, as long as there is a constrained geometry catalyst in at least one reactor, such as disclosed in U.S. patent application Ser. Nos. 08/208,068 filed Mar. 8, 1994 and 08/510,527 filed Aug. 2, 1995.

The constrained geometry catalysts may be used singularly, in combination with other constrained geometry catalysts (e.g., different species, such as use of different metal atoms, different ligands, or different co-catalysts, may be used in various combinations), or in conjunction with Ziegler-type catalysts in separate reactors connected in parallel or in series. The Ziegler catalyst is generally a titanium based complex suitably prepared for use as a catalyst for the gas phase polymerization of olefins. Representative Ziegler catalysts that can be used in this invention include those comprising a (i) solid support component derived from a magnesium halide and/or silica, and (ii) one or more of a transition metal component represented by the formulae $TrX''_{4-r}(OR^1)_r$; $TrX''_{4-r}R^2_r$; $VOX''_3$ and $VO(OR^1)_3$, in which:

Tr is a Group IVB, VB or VIB metal, r is 0 or a number equal to or less than 4,

X'' is a halogen, $R^1$ is an alkyl, aryl or cycloalkyl group having from 1 to 20 carbon atoms, and $R^2$ is an alkyl, aryl, aralkyl or substituted aralkyl group.

These complexes are further described and methods for their preparation are disclosed in U.S. Pat. Nos. 4,302,565, 4,302,566, 4,303,771, 4,395,359, 4,405,495, 4,481,301, and 4,562,169 all of which are incorporated by reference.

The polymerization in each reactor is conducted in the gas phase using a continuous fluidized bed process. A typical fluidized bed reactor is described in U.S. Pat. No. 4,482,687 which is incorporated by reference. As noted, the reactors may be connected in series as taught in U.S. Pat. Nos. 5,047,468, 5,126,398, and 5,149,738. While two reactors are preferred, three or more reactors can be used to further vary the molecular weight distribution. As more reactors are added producing copolymers with different average molecular weight distributions, however, the sharp diversity of which two reactors are capable becomes less and less apparent. These additional reactors can be used to produce copolymers with melt indices or densities, intermediate to the high and low melt indices previously described.

As noted previously, two or more reactors may be run in parallel with the resulting polymeric product being blended. This permits the reactors to be run independently, with different catalysts, different amounts of ethylene and alpha-olefins, different recycle rates and at different productivity rates. The various melt indices can be prepared in any order, i.e., in any reactor in the series. For example, the low melt index copolymer can be made in the first or second reactor in the series and the high melt index copolymer can be made in the first or second reactor as well. The actual conditions used will depend on the comonomer used and the desired copolymer properties and are readily ascertained by the skilled artisan.

The constrained geometry catalyst, the ethylene monomer, any comonomers and hydrogen, if any, are continuously fed into each reactor and ethylene copolymer and active catalyst are continuously removed from one reactor and introduced into the next reactor. The product is continuously removed from the last reactor in the series.

The α-olefins used in this aspect of the invention are the same as those that have been previously described in this application. Preferred α-olefins are 1-butene, propylene, 1-hexene, 1-octene, 1-pentene, and 4-methyl-1-pentene.

Supported Catalysts

Supported catalyst complexes such as those taught in pending U.S. application Ser. No. 08/626,303 filed Apr. 1, 1996, which is incorporated herein by reference, can be used in the process taught by applicants.

The Catalyst Support

Typically, the support can be any of the known solid catalyst supports, particularly porous supports, such as talc, inorganic oxides, and resinous support materials such as polyolefins. Preferably, the support material is an inorganic oxide in particulate form.

Suitable inorganic oxide materials which are desirably employed in accordance with this invention include Group 2, 3, 4, 13, or 14 metal oxides. The most preferred catalyst support materials include silica, alumina, and silica-alumina, and mixtures thereof. Other inorganic oxides that may be employed either alone or in combination with the silica, alumina, or silica-alumina are magnesia, titania, zirconia. Other suitable support materials, however, can be employed, for example, finely divided polyolefins such as finely divided polyethylene.

The specific particle size, surface area and pore volume of the inorganic oxide determine the amount of oxide that is desirable to employ in preparing the catalyst compositions, as well as affecting the properties of the polymer formed. These properties must frequently be taken into consideration in choosing an inorganic oxide for use in a particular aspect of the invention. In general, optimum results are usually obtained by the use of inorganic oxides having an average particle size in the range of about 20 to 200 microns, preferably about 40 to 100 microns, more preferably 50 to 80 microns; a surface area of about 50 to 1,000 square meters per gram, preferably about 100 to 400 square meters per gram; and a pore volume of about 0.5 to 3.5 cc per gram; preferably about 0.5 to 2 cc per gram.

The inorganic oxide support used in the preparation of the catalyst may be any particulate oxide or mixed oxide such that it is substantially free of adsorbed moisture or surface hydroxyl groups. If a support is employed that contains surface hydroxyl groups, a drying or dehydration treatment must be employed. Timing for the dehydration of the support is not critical, i.e., dehydration may occur immediately before use of the support or days before provided once the support is dehydrated, it is protected from moisture and impurities. Thermal treatment to dehydrate the support may be carried out in vacuum or while purging with a dry inert gas such as nitrogen at a temperature of 100 C to 1000 C, and.preferably, above 300 C to 900 C, or more preferably 500 C to 850 C. Pressure considerations are not critical. The duration of the thermal treatment can be for a period of 1–100 hours, preferably 2–24 hours.

In one embodiment, chemical dehydration or chemical treatment to dehydrate the support may be accomplished by slurrying the inorganic particulate material, such as, for example, silica in an inert low boiling hydrocarbon, such as, for example, silica in an inert low boiling hydrocarbon, such as, for example, hexane. During the chemical dehydration reaction, the support, preferably silica, should be maintained in a moisture and oxygen-free atmosphere. To the silica slurry is then added a low boiling inert hydrocarbon solution of the chemical dehydrating agent. Useful chemical agents are for example, active silanes, such as trimethylchlorosilane or hexamethyldisilazane and alkyl metal compounds such as dibutylmagnesium, diethylzine, trimethylaluminum, triethylaluminum, trimethylaluminum and triethylaluminum being particularly preferred. The ratio of millimoles of metal alkyl per gram of support may be between 0.1 to 100, a ratio of 1 to 10 being preferred. The chemical dehydration may be carried out at temperatures of –100 C to 300 C (preferably 0 C to 100 C) and contact times can range from 1 minute to 48 hours, preferably 15 minutes to 2 hours. The treated silica is filtered off and washed with an aromatic solvent, such as toluene or xylenes, to remove any activating amounts of possibly formed alumoxanes, then optionally washed with a light aliphatic hydrocarbon (pentanes or hexanes) before drying in vacuo or in dry stream of inert gas.

In another embodiment, the catalyst support may be readily made by the reaction of $SiO_2$ and an alumoxane (modified or unmodified) in an inert solvent, under an inert atmosphere, preferably argon or nitrogen, and under anhydrous conditions. Such reaction conditions are well known. Suitable inert solvents include aliphatic or aromatic organic solvents.

While the order of addition of the $SiO_2$ and alumoxane and solvent is not critical in preparing the catalyst support, preferably the alumoxane is added to a slurry of $SiO_2$ in the inert solvent. The $SiO_2$ and alumoxane mixture is preferably stirred throughout the reaction in order to expedite the reaction process by providing and maintaining an intimate contact between the reactants.

The reaction between $SiO_2$ and alumoxane in making the catalyst support of this invention may be performed at temperatures between about –20° C. and about 120° C., preferably between about 0° C. and about 100° C., more preferably between about 20° C. and about 80° C., and most preferably between about 40° C. and about 70° C., all preferably at about atmospheric pressure. The time of the reaction between $SiO_2$ and alumoxane may be from about 15 minutes (min) to about 24 hours, preferably from about 30 min to about 12 hours, more preferably from about 1 hour to about 8 hours, and most preferably from about 2 hours to about 4 hours, in accordance with the conditions of temperature and pressure set forth above. The resulting reaction product is then washed to remove excess alumoxane and dried leaving an adduct of alumoxane and silica.

While it is most preferred that the $SiO_2$ is reacted to saturation with an alumoxane, less than full saturation of the $SiO_2$ is operable in the process of this invention; however, the resultant supported catalyst is expected to operate at less than optimal efficiency.

After the catalyst support is prepared, then typically it is either combined with a metal complex and an activating cocatalyst, or it is combined the with a metal complex previously activated by an activating technique.

In order that persons skilled in the art may better understand the practice of supporting homogeneous catalysts for the practice of the present invention, the following examples are provided by way of illustration, and not by way of limitation. Additional information which may be useful in state of the art practice may be found in each of the references cited herein, which are incorporated by reference.

Experimental

All polymerizations, unless otherwise noted, were carried out under nitrogen pressures of 20–80 psi in a 6 liter gas phase reactor having a four inch diameter thirty inch long fluidization zone and an eight inch diameter ten inch long velocity reduction zone which are connected by a transition section having tapered walls. Typical operating ranges are 40 to 100° C., 250 to 350 psia, and up to 8 hours reaction time. Ethylene, comonomer (if used), and hydrogen enter the bottom of the reactor where they pass through a gas distributor plate, The flow of the gas is 2 to 8 times the minimum particle fluidization velocity, *Fluidization Engineering*, 2nd Ed., D. Kunii and O. Levenspiel, 1991, Butterworth-Heinemann. Most of the suspended solids disengage in the velocity reduction zone. The reactant gases exit the top of the fluidization zone and pass through a dust filter to remove any fines. The oases then pass through a gas booster pump. The polymer is allowed to accumulate in the reactor over the course of the reaction. The total system pressure is kept constant during the reaction by regulating the flow of the ethylene into the reactor. Polymer is removed from the reactor to a recovery vessel by opening a valve located at the bottom of the fluidization zone. The polymer recovery vessel is kept at a lower pressure than the reactor. The pressures of ethylene, comonomer and hydrogen reported refer to partial pressures. The polyethylene powders used as supports were high density homopolymers. The titanium complex, $(C_5Me_4SiMe_2NCMe_3)TiMe_2$ is prepared according to U.S. Pat. No. 5,189,192, which is incorporated by reference, and the borane complex, $B(C_6F_5)_3$ is prepared according to the procedure taught in Z. Naturforsch. 20b, 5–11 (1965).

Prior to being used as supports, the silicas were treated with the aluminum alkyl, triethylaluminum (TEA). The purpose of this pretreatment was to remove from the silica any residual water and/or hydroxyl groups. Following the pretreatment, the silicas were then washed several times with toluene to remove any residual TEA or alumoxane which may have resulted during the dehydration process. The supports were then dried under reduced pressure. In some cases the supports were washed with hexane before drying. Any amount of alumoxane which may have remained on the silica was present in a non-activating amount (see Examples 20 and 21).

EXAMPLE 1

Catalyst/Support Preparation

An aliquot (4 mL) of a 0.005 M solution (60 μmol) of $(C_5Me_4SiMe_2NCMe_3)TiMe_2$ in toluene and 4.8 mL of a 0.005 M solution (60 μmol) of $B(C_6F_5)_3$ in toluene were stirred with 0.640 g of high density polyethylene powder having zero melt index which previously had been sieved to remove any particles larger than 25 mesh. The solvent was removed to give a pale yellowish free-flowing powder. The resulting catalyst composition was divided into two portions, each weighing about 0.32 g.

Polymerization

One portion of the catalyst prepared above was added to the reactor which was under ethylene and hydrogen pressures of 270 psi and 0.8 psi (0.3 mol %), respectively, at a temperature of 57° C. A 2° C. exotherm was observed. After 1 hour, the second portion of catalyst was added. A 9° C. exotherm was observed. The yield of polymer having a 11.24 melt index was 26 g.

EXAMPLE 2

Catalyst/Support Preparation

A polyethylene-supported catalyst was formed analogously to Example 1, except that 40 μmol each of the titanium complex and the borane complex and 0.600 g of polyethylene powder having zero melt index were used. The resulting catalyst composition was divided into two portions, each weighing about 0.30 g.

Polymerization

In a manner similar to Example 1, one portion of the catalyst prepared above was added to the reactor which was under ethylene and hydrogen pressures of 250 psi and 0.55 psi (0.22 mol %), respectively, at a temperature of 69° C. A 1° C. exotherm was observed. After about one half hour, the second portion of catalyst was added. A 74° C. exotherm was observed. The polymer was removed in two portions, 19 g of polymer powder having a melt index of 0.185, and 21.3 g of pieces of polymer having a melt index of 0.575 which had the appearance of having been melted.

EXAMPLE 3

Catalyst/Support Preparation

In a manner substantially the same as in Example 1, except that 2 mL (10 μmol) of the $(C_5Me_4SiMe_2NCMe_3)TiMe_2$ solution and 2.4 mL (12 μmol) of the $B(C_6F_5)_3$ solution were combined with 0.600 g of 11.4 melt index polyethylene powder to prepare the supported catalyst. 0.30 g of the resulting supported catalyst (5 μmol titanium complex, 6 μmol borane complex) was used in the following polymerization.

Polymerization

The polymerization was carried out in two stages, similar to Example 2, except that the ethylene pressure was 300 psi. No hydrogen was present during the polymerization. The initial temperature was 61° C. The second portion of catalyst was added about 1 hour after the first portion of catalyst had been added. The yield of granular polymer having a melt index of zero was 25.4 g.

EXAMPLE 4

Catalyst/Support Preparation

A polyethylene-supported catalyst was formed analogous to Example 3, except that 0.59 melt index polyethylene and 12 μmol of the borane complex were used.

Polymerization

The polymerization was carried out analogous to Example 3, except that the ethylene pressure was 290 psi. No hydrogen was present during the polymerization. The initial temperature was 66° C. An exotherm of 4° C. was observed on addition of the first portion of catalyst. An exotherm of 24° C. was observed on addition of the second portion of catalyst. The yield of granular polymer having a melt index of zero was 43.9 g.

EXAMPLE 5

Catalyst/Support Preparation

An aliquot (4 mL) of a 0.005 M solution (20 μmol) of $(C_5Me_4SiMe_2NCMe_3)TiMe_2$ in toluene and 4.8 mL of a 0.005 M solution (24 µmol) of $B(C_6F_5)_3$ in toluene were stirred with 0.600 g of 0.33 melt index high density polyethylene powder which previously had been sieved to remove any particles larger than 25 mesh. The solvent was removed to give a pale yellowish free-flowing powder.

Polymerization

An amount (0.30 g; 10 µmol titanium complex, 12 µmol borane complex) of the solid supported catalyst was introduced into a fluidized bed reactor pressurized to 260 psi ethylene containing 0.25 mol % (based on ethylene 0.65 psi) hydrogen at a temperature of 53° C. After a run time of 5 hours 81 g of polyethylene saving a melt index of 1.30 was removed. The productivity was 169,000 g polymer/g Ti.

EXAMPLE 6

Catalyst/Support Preparation

In a manner substantially the same as in Comparative Example 1, except that 2 mL (10 µmol) of the $(C_5Me_4SiMe_2NCMe_3)TiMe_2$ solution and 2.4 mL (12 µmol) of the $B(C_6F_5)_3$ solution were combined with 0.600 g of 0.33 melt index polyethylene powder to prepare the supported catalyst. 0.30 g of the resulting supported catalyst (5 µmol titanium complex, 6 µmol borane complex) was used in the following polymerization.

Polymerization

The polymerization was carried out as in Example 5, except that the ethylene and hydrogen pressures were 230 psi and 0.46 psi (0.20 mol %), respectively, at a temperature of 47° C. The yield of polymer having a melt index of 0.65 was 27.0 g.

EXAMPLE 7

Polymerization

The polymerization was carried out as in Example 6, except that the ethylene and hydrogen pressures were 280 psi and 1.4 psi (0.50 mol %), respectively, at a temperature of 55° C. The yield of polymer having a melt index of 17.3 was 11.6 g.

EXAMPLE 8

Catalyst/Support Preparation 2 mL of a 0.005 M solution (10 µmol) of $(C_5Me_4SiMe_2NCMe_3)TiMe_2$ and 2 mL of a 0.005 M solution (10 µmol) of $B(C_6F_5)_3$ were combined in a Fisher-Porter bottle with 0.501 g Davison 952 silica (dried at 900° C. for 4 hours under an oxygen stream, then cooled under a stream of nitrogen) and 30–40 mL pentane. The container was pressurized with 6 psi ethylene for 2 hours. The solvent was removed to give a dry prepolymer support. To 0.500 g of the supported polymer were added 4 mL of a 0.005 M solution (20 µmol) of $(C_5Me_4SiMe_2NCMe_3)TiMe_2$ and 4 mL of a 0.005 M solution (20 µmol) of $B(C_6F_5)_3$. The solvent was removed to give a dry powder.

Polymerization

Using the catalyst/support prepared above, the polymerization was carried out in a manner similar to Example 5, except that the ethylene and hydrogen pressures were 270 psi and 0.3 psi (0.30 mol %), respectively, at a temperature of 60° C. The yield of polymer having a melt index of 3.0 was 30.4 g.

EXAMPLES 9–19

A summary of Examples 9–19 is given in Table 1. Several different silicas were used as supports throughout these Examples: Davison types 952 and 951, Davison type 03, Calsicat type D and Shell type 980-H. Included in Table 1 are the individual run parameters (catalyst level, temperature, monomer particle pressures, silica type and silica pretreatment) along with the resulting polymer's density, $I_2$, $I_{10}/I_2$ and molecular weight distribution (MWD).

Support Preparation

The silicas were pretreated prior to catalyst addition with triethylaluminum (TEA). The pretreatment procedure involved first adding 2.0 g of silica to 25 mL of toluene. The amount of TEA indicated in Table 1 was then added by syringe to the stirred silica slurry. Stirring was continued for at least 15 minutes. The solids were then filtered and washed several times with toluene to remove any residual TEA. The treated silica was then dried under vacuum.

Preparation of the Supported Catalyst

Appropriate amounts, as indicated in Table 1, of 0.005 M or of 0.010 M solutions of $B(C_6F_5)_3$ in toluene and of very pale yellow 0.005 M solutions of $(C_5Me_4SiMe_2NCMe_3)TiMe_2$ in hexane were added to 0.125 g of stirred silica to give bright yellow slurries. The solvents were then removed under vacuum from the stirred slurries to give the catalysts as free flowing powders.

General Polymerization Procedure

All amounts of support catalyst, titanium loading and borane, pressures of ethylene, 1-butene and hydrogen, reactor temperatures and run times and reaction yields are indicated in Table 1. The given amounts of the solid supported catalyst were introduced into the fluidized bed reactor pressured to 300 psi with nitrogen, ethylene, 1-butene and hydrogen. After the indicated run times, the polymers were removed from the reactor by venting the pressurized contents into a recovery vessel.

EXAMPLE 20

Catalyst/Support Preparation

Davison 952 silica was pretreated as in Examples 9–19 under "Support preparation" using 0.5 mL of TEA and 2.0 g silica.

The catalyst was prepared as in Examples 9–19 under "Preparation of the Supported Catalyst" using 3 µmole of $(C_5Me_4SiMe_2NCMe_3)TiMe_2$, 9 µmole of $B(C_6F_5)_3$ and 0.10 g of the above treated silica.

Polymerization

The solid supported catalyst was introduced into the fluidized bed reactor pressurized with 240 psi ethylene, 9 psi 1-butene, 1.2 psi hydrogen and 51 psi nitrogen. The initial temperature was 74 C and the run time was 78 minutes. The yield of granular powder was 5.5 g.

EXAMPLE 21

Catalyst/Support Preparation

Using the silica of Example 20, the silica-supported catalyst was prepared analogously to Example 20 except that none of the borane complex was added to the support.

Polymerization

The solid supported catalyst was introduced into the fluidized bed reactor pressurized with 240 psi ethylene, 9 psi 1-butene, 1.2 psi hydrogen and 51 psi nitrogen. The initial temperature was 75 C and the run time was 75 minutes. No polymer was recovered from the reactor, indicating that any aluminum compounds possibly remaining after washing the silica to remove residual TEA are only present at non-activating levels.

EXAMPLE 22

Catalyst/Support Preparation

Preparation of the supported catalyst was analogous to Example 20 except that 12 μmole of $B(C_6F_5)_3$ and 4 μmole of $(C_5Me_4SiMe_2NCMe_3)TiMe_2$, were added to 0.20 g of the treated silica.

Polymerization

The solid supported catalyst was introduced into the fluidized bed reactor pressurized with 240 psi ethylene, 1.5 psi, 1,5-hexadiene, 1.2 psi hydrogen, and 60 psi nitrogen. The initial temperature was 76 C and the run time was 126 minutes. 21 g of free flowing polymer powder were removed.

EXAMPLE 23

Catalyst/Support Preparation

The supported catalyst was prepared analogously to Example 22.

Polymerization

The solid supported catalyst was introduced into the fluidized bed reactor pressurized with 240 psi ethylene, 0.75 psi 1,5-hexadiene, 1.2 psi hydrogen, and 60 pis nitrogen. The initial temperature was 80 C and the run time was 187 minutes. 11.6 g of free flowing polymer powder were removed.

EXAMPLE 24

Catalyst/Support Preparation

Preparation of the supported catalyst was analogous to Example 20 except that 9 μmole of $B(C_6F_5)_3$, 3 μmole of $(C_5Me_4SiMe_2NCMe_3)TiMe_2$, and 0.10 g of the treated silica were used.

Polymerization

The solid supported catalyst was introduced into the fluidized bed reactor pressurized with 240 psi ethylene, 6 psi 1-butene, 0.75 psi 1,7-octadiene, 1.2 psi hydrogen, and 60 psi nitrogen. The initial temperature was 80 C and the run time was 74 minutes. 14.4 g of free flowing polymer powder were removed.

EXAMPLE 25

Catalyst/Support Preparation

The supported catalyst was prepared analogously to Example 24.

Polymerization

The solid supported catalyst was introduces into the fluidized bed reactor pressurized with 240 psi ethylene, 6 psi 1-butene, 0.38 psi 1,7-octadiene, 1.2 psi hydrogen, and 60 psi nitrogen. The initial temperature was 70 C and the run time was 99 minutes. 12.1 g of free flowing polymer powder were removed.

TABLE 1

Summary of gas phase polymerization results

| Example No. | μmoles | | partial press. (psi) | | | silica+ | ml-NTEA◇/ g silica | temp (C.) | yield (g) | time (min) | density (g/cc) | $I_2$ | MWD | $I_{10}/I_2$ |
|---|---|---|---|---|---|---|---|---|---|---|---|---|---|---|
| | Ti | borane | $C_2H_4$* | $C_4H_8$** | $H_2$*** | | | | | | | | | |
| 9  | 1 | 3 | 240 | 6  | 1.2 | D952  | 0.25 | 71 | 6.3  | 93  | 0.9283 | 1.9 | 2.56 | 7.4  |
| 10 | 2 | 0 | 240 | 6  | 1.2 | D952  | 0.25 | 70 | 25.7 | 67  | 0.9203 | 1.5 | 2.49 | 7.3  |
| 11 | 2 | 6 | 240 | 6  | 1.2 | D952  | 0.25 | 65 | 7.9  | 68  | 0.9232 | 1.8 | 2.43 | 7.7  |
| 12 | 2 | 6 | 240 | 6  | 1.2 | D952  | 0.50 | 69 | 23.9 | 98  | 0.9179 | 1.4 | 2.55 | 7.7  |
| 13 | 2 | 6 | 240 | 12 | 1.2 | D952  | 0.25 | 68 | 38.9 | 53  | 0.9070 | 0.4 | 2.33 | 8.7  |
| 14 | 1 | 3 | 240 | 12 | 1.2 | D03   | 0.50 | 69 | 27.2 | 69  | 0.8979 | 0.2 | 1.98 | 10.9 |
| 15 | 1 | 3 | 240 | 6  | 1.2 | D03   | 0.50 | 69 | 24.8 | 16  | 0.9078 | 0.4 | 2.23 | 9.3  |
| 16 | 2 | 6 | 240 | 6  | 1.4 | D951  | 0.25 | 73 | 5.1  | 61  | 0.9276 | 2.3 | 2.52 | 8.0  |
| 17 | 2 | 6 | 240 | 6  | 1.4 | Sh980 | 0.25 | 67 | 11.7 | 77  | 0.9283 | 2.5 | 2.45 | 8.0  |
| 18 | 2 | 6 | 240 | 6  | 1.4 | Sh980 | 0.25 | 71 | 15.4 | 102 | 0.9243 | 2.4 | 2.49 | 7.8  |
| 19 | 1 | 3 | 24D | 6  | 1.2 | Cal D | 0.25 | 68 | 5.4  | 92  | 0.9233 | 1.4 | 2.55 | 7.9  |

*$C_2H_4$ refers to ethylene partial pressure
**$C_4H_8$ refers to 1-butene partial pressure
***$H_2$ refers to hydrogen partial pressure
+silica: D952, D03 and D951 refer to Davison silica types 952, 03 and 951 respectively; Sh980H refers to Shell silica type 980-H; Cal D refers to Calsicat silica type D.
◇ NTEA refers to neat triethylaluminum.

The MWDs of the polymers from Examples 9–19 as shown in Table 1, were relatively narrow ranging in value from 1.98 to 2.56, in contrast to the work of Canich et al in U.S. Pat. No. 5,057,475 where reported MWDs ranged from 2.67 to 5.00 (4.817 for copolymer of ethylene and hexene in Example 8). Table 1 shows that ethylene or ethylene/α-olefin polymers can be made where the $I_{10}/I_2$ increases without increasing MWD.

Although this invention has been described in considerable detail through the preceding examples, such detail is for the purpose of illustration and is not to be construed necessarily as a limitation upon the invention. Many variations can be made upon the preceding examples without departing from the spirit and scope of the invention as described in the following claims.

We claim:

1. A fluidized bed, gas phase process for the production of an ethylene polymer having long chain branching and a critical shear stress at the onset of gross melt fracture of greater than about $4\times10^6$ dyne/cm$^2$, the process comprising the steps of:

(A) feeding gaseous monomers into a fluidized bed reactor and contacting the monomers under continuous polymerization conditions in the reactor, the gaseous monomers comprising at least one of (i) ethylene, or (ii) ethylene and at least one of a copolymerizable alpha-olefin or diolefin, in the presence of a catalyst prepared from:

1. a metal complex corresponding to the formula:

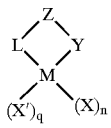

wherein:
M is a Group 4 metal in the +2, +3 or +4 formal oxidation state;
L is a group containing a cyclic, delocalized, aromatic, anionic, system through which the L group is bound to M, and which L group is also bound to Z, said L group containing up to 60 nonhydrogen atoms;
Z is a moiety covalently bound to both L and Y, comprising boron, or a member of Group 14 of the Periodic Table of the Elements, said moiety having up to 60 nonhydrogen atoms;
Y is a moiety comprising nitrogen, phosphorus, sulfur or oxygen through which Y is covalently bound to both Z and M, said moiety having up to 25 nonhydrogen atoms;
X' independently each occurrence is a Lewis base containing up to 40 nonhydrogen atoms;
X independently each occurrence is a monovalent anionic moiety having up to 20 nonhydrogen atoms, provided however that neither X is an aromatic group that is Π-bonded to M, optionally, two X groups may be covalently bound together forming a divalent dianionic moiety having both valences bound to M, or further optionally one or more X and one X' group may be bonded together thereby forming a moiety that is both covalently bound to M and coordinated thereto by means of Lewis base functionality;
q is a number from 0 to 1; and
n is 0, 1 or 2 depending on the formal oxidation state of M;

2. an activating cocatalyst selected from the group consisting of neutral Lewis acids and nonpolymeric, compatible noncoordinating ion forming compounds; and 3. a support;

(B) withdrawing continuously from the reactor unreacted gaseous monomers, and forming from the withdrawn unreacted gaseous monomers a recycle stream;

(C) feeding the recycle stream to the reactor;

(D) producing in the reactor from the gaseous monomers an ethylene polymer having long chain branching; and (E) recovering the ethylene polymer having long chain branching from the reactor.

2. The process according to claim 1 wherein M is titanium and X each occurence is a monovalent ligand group of up to 20 nonhydrogen atoms.

3. The process according to claim 2 wherein X is a $C_{1-20}$ hydrocarbyl group or wherein n is 2 and the two X groups form a hydrocarbadiyl group.

4. The process according to claim 1 wherein the ethylene polymer has long chain branching, and contains $\geq 80$ mol percent of ethylene and $\leq 20$ mol percent of one or more $C_3$–$C_8$ alpha-olefin or diolefin comonomers.

5. The process according to claim 1 wherein the support is silica, alumina, clay, cornstarch, talc or polyethylene, or a mixture thereof.

6. The process according to claim 1 wherein Y is —O—, —S—, —NR*—, —PR*— and R* is independently a hydrocarbyl or silyl group having up to 12 nonhydrogen atoms.

7. The process according to claim 1 in which the activating cocatalyst is an alumoxane.

8. The process according to claim 1 in which the activating cocatalyst is a modified alumoxane.

9. The process according to claim 1 wherein the activating cocatalyst is a tris(pentafluorophenyl)borane.

10. The process according to claim 2 wherein X is methyl or benzyl.

11. The process according to claim 1 wherein said process is conducted in at least two fluidized bed gas phase reactors connected in parallel.

12. The process according to claim 1 wherein said process is conducted in at least two fluidized bed gas phase reactors connected in series.

13. The process of claim 1 conducted in at least two fluidized bed gas phase reactors, one reactor of which contains a supported Ziegler catalyst.

14. The process of claim 1 conducted in a single fluidized bed gas phase reactor.

15. The process of claim 14 in which the reactor contains two different species of the catalyst.

16. The process of claim 1 in which the process is conducted in a fluidized bed gas phase reactor which is coupled to a slurry phase reactor.

17. The process of claim 5 in which the support is pretreated.

18. A fluidized bed, gas phase process for the production of an ethylene polymer having long chain branching and a critical shear stress at the onset of gross melt fracture of greater than about $4\times10^6$ dyne/cm$^2$, the process comprising the steps of:

(A) feeding gaseous monomers into a fluidized bed reactor and contacting the monomers under continuous polymerization conditions in the reactor, the gaseous monomers comprising at least one of (i) ethylene, or (ii) ethylene and at least one of a copolymerizable alpha-olefin or diolefin, in the presence of a catalyst prepared from:

1. a metal complex corresponding to the formula

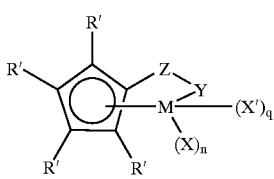 (I)

wherein:
R' each occurrence is independently selected from the group consisting of hydrogen, alkyl, aryl, silyl, and combinations thereof having up to 20 nonhydrogen atoms;
X each occurrence independently is selected from the group consisting of hydride, alkyl, aryl, silyl and combinations thereof, having up to 20 nonhydrogen atoms;
Y is a divalent ligand group comprising nitrogen, phosphorus, oxygen or sulfur and having up to 20 nonhydrogen atoms, said Y being bonded to Z and M through said nitrogen, phosphorus, oxygen or sulfur, and optionally Y and Z together form a fused ring system;
M is Ti, Zr, or Hf,
Z is $SiR^*_2$, $CR^*_2$, $SiR^*_2SiR^*_2$, $CR^*_2CR^*_2$, $CR^*=CR^*$, or $CR^*_2SiR^*_2$;
R* each occurrence is independently selected from the group consisting of hydrogen, alkyl, aryl, silyl, halogenated alkyl, halogenated aryl groups having up to 20 nonhydrogen atoms, and mixtures thereof, or two or more R* groups from Y, Z, or from Z together with Y form a fused ring system;
X' is 1,4-diphenylbutadiene or 1,3-pentadiene;
q is 0 or 1;
n is 0, 1 or 2;
2. an activating cocatalyst selected from the group consisting of neutral Lewis acids and nonpolymeric, compatible noncoordinating ion forming compounds; and
3. a support;
(B) withdrawing continuously from the reactor unreacted gaseous monomers, and forming from the withdrawn unreacted gaseous monomers a recycle stream;
(C) feeding the recycle stream to the reactor;
(D) producing in the reactor from the gaseous monomers an ethylene polymer having long chain branching; and
(E) recovering the ethylene polymer having long chain branching from the reactor.

19. The process of claim 18, wherein M is titanium.

20. The process of claim 18, wherein X is a $C_{1-20}$ hydrocarbyl group.

21. A fluidized bed, gas phase process for the production of an ethylene polymer having long chain branching, the process comprising the steps of:
(A) feeding gaseous monomers into a fluidized bed reactor and contacting the monomers under continuous polymerization conditions in the reactor, the gaseous monomers comprising at least one of (i) ethylene, or (ii) ethylene and at least one of a copolymerizable alpha-olefin or diolefin, in the presence of a supported catalyst activated through the use of an activating technique, and prepared from:
1. a metal complex corresponding to the formula:

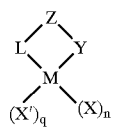

wherein:
M is a Group 4 metal in the +2, +3 or +4 formal oxidation state;
L is a group containing a cyclic, delocalized, aromatic, anionic, π-system through which the L group is bound to M, and which L group is also bound to Z, said L group containing up to 60 nonhydrogen atoms;
Z is a moiety covalently bound to both L and Y, comprising boron, or a member of Group 14 of the Periodic Table of the Elements, said moiety having up to 60 nonhydrogen atoms;
Y is a moiety comprising nitrogen, phosphorus, sulfur or oxygen through which Y is covalently bound to both Z and M, said moiety having up to 25 nonhydrogen atoms;
X' independently each occurrence is a Lewis base containing up to 40 nonhydrogen atoms;
X independently each occurrence is a monovalent anionic moiety having up to 20 nonhydrogen atoms, provided however that neither X is an aromatic group that is π-bonded to M, optionally, two X groups may be covalently bound together forming a divalent dianionic moiety having both valences bound to M, or further optionally one or more X and one X' group may be bonded together thereby forming a moiety that is both covalently bound to M and coordinated thereto by means of Lewis base functionality;
q is a number from 0 to 1; and
n is 1 or 2 depending on the formal oxidation state of M; and
2. a support;
(B) withdrawing continuously from the reactor unreacted gaseous monomers, and forming from the withdrawn unreacted gaseous monomers a recycle stream;
(C) feeding the recycle stream to the reactor;
(D) producing in the reactor from the gaseous monomers an ethylene polymer having long chain branching; and
(E) recovering the ethylene polymer having long chain branching from the reactor.

22. The process of claim 21, wherein M is titanium.

23. The process of claim 21, wherein X is a $C_{1-20}$ hydrocarbyl group.

24. The process of claim 21, which the activating technique is electrochemical oxidation of the metal complex under electrolysis conditions in the presence of a supporting electrolyte comprising a noncoordinating, inert anion.

* * * * *